(12) United States Patent
Poinsard

(10) Patent No.: US 9,732,044 B2
(45) Date of Patent: Aug. 15, 2017

(54) N-(PYRID-4-YL)AMIDES AND N-(PYRIMIDIN-4-YL)AMIDES AND THEIR PHARMACEUTICAL AND COSMETIC USE

(71) Applicant: GALDERMA RESEARCH & DEVELOPMENT, Biot (FR)

(72) Inventor: Cédric Poinsard, Le Rouret (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/237,236

(22) Filed: Aug. 15, 2016

(65) Prior Publication Data
US 2017/0066725 A1 Mar. 9, 2017

Related U.S. Application Data

(62) Division of application No. 14/355,810, filed as application No. PCT/EP2012/071811 on Nov. 5, 2012, now Pat. No. 9,452,120.

(60) Provisional application No. 61/555,583, filed on Nov. 4, 2011.

(30) Foreign Application Priority Data

Nov. 4, 2011 (FR) ..................................... 11 59997

(51) Int. Cl.
| | |
|---|---|
| C07D 239/47 | (2006.01) |
| A61K 31/505 | (2006.01) |
| C07D 213/81 | (2006.01) |
| A61Q 7/00 | (2006.01) |
| C07D 213/75 | (2006.01) |
| C07D 405/12 | (2006.01) |
| C07D 239/52 | (2006.01) |
| C07D 239/48 | (2006.01) |
| A61K 8/49 | (2006.01) |
| A61Q 7/02 | (2006.01) |
| A61K 8/69 | (2006.01) |
| A61Q 19/00 | (2006.01) |
| C07D 213/79 | (2006.01) |
| C07D 213/84 | (2006.01) |
| A61Q 5/00 | (2006.01) |

(52) U.S. Cl.
CPC ............ *C07D 239/47* (2013.01); *A61K 8/498* (2013.01); *A61K 8/4926* (2013.01); *A61K 8/4953* (2013.01); *A61K 8/69* (2013.01); *A61Q 5/008* (2013.01); *A61Q 7/00* (2013.01); *A61Q 7/02* (2013.01); *A61Q 19/008* (2013.01); *C07D 213/75* (2013.01); *C07D 213/79* (2013.01); *C07D 213/81* (2013.01); *C07D 213/84* (2013.01); *C07D 239/48* (2013.01); *C07D 239/52* (2013.01); *C07D 405/12* (2013.01)

(58) Field of Classification Search
CPC .. C07D 239/42; C07D 239/46; C07D 239/47; C07D 239/52; A61K 31/505
USPC .................. 544/312, 319, 329; 514/256, 269
See application file for complete search history.

(56) References Cited

U.S. PATENT DOCUMENTS

| | | |
|---|---|---|
| 3,039,930 A | 6/1962 | Gray |
| 2004/0224992 A1 | 11/2004 | Cywin et al. |
| 2006/0287326 A1 | 12/2006 | Dankulich et al. |

FOREIGN PATENT DOCUMENTS

| | | |
|---|---|---|
| EP | 0079191 A1 | 5/1983 |
| FR | 2954316 A1 | 6/2011 |
| WO | 2004/035737 A2 | 4/2004 |
| WO | 2004/064747 A2 | 8/2004 |

OTHER PUBLICATIONS

Brownlie, CAPLUS Abstract 45:15745 (1951).*

(Continued)

*Primary Examiner* — Deepak Rao
(74) *Attorney, Agent, or Firm* — Dentons US LLP

(57) ABSTRACT

The present invention relates generally to the field of pharmaceuticals and cosmetics. More specifically, the present invention pertains to certain N-(pyrid-4-yl)amides and N-(pyrimidin-4-yl)amides of the following formula which are potent modulators (e.g., inhibitors) of an androgen receptor, and which are useful, for example, in therapy, for example, in the treatment of a dermatological disease or disorder; a disease or disorder of the sebaceous gland(s); acne; hyperseborrhoea; oily skin; seborrhoeic dermatitis; hyperpilosity or hirsutism; atopic dermatitis; or androgenic alopecia; especially acne. The present invention also relates to compositions (e.g., pharmaceutical compositions, cosmetic compositions) comprising the compounds; methods of preparing the compositions; methods of modulating (e.g., inhibiting) an androgen receptor using the compounds and/or compositions; and medical and/or cosmetic use of the compounds and compositions.

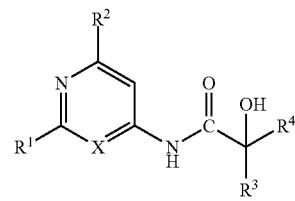

18 Claims, No Drawings

(56) References Cited

OTHER PUBLICATIONS

Vinkers et al., CAPLUS Abstract 139:110999 (2003).*
International Search Report and Written Opinion dated Nov. 27, 2012 corresponding to International Patent Application No. PCT/EP2012/071811, 3 pages.
Muro et al., CAPLUS Abstract 107:115499 (English Language abstract for JP 62-89679). 1987.

* cited by examiner

US 9,732,044 B2

N-(PYRID-4-YL)AMIDES AND N-(PYRIMIDIN-4-YL)AMIDES AND THEIR PHARMACEUTICAL AND COSMETIC USE

RELATED APPLICATIONS

This application is a continuation of U.S. patent application Ser. No. 14/355,810, filed on May 1, 2014, now U.S. Pat. No. 9,452,120, which is the National Stage Entry of PCT/EP2012/071811, filed on Nov. 5, 2012, and designating the United States (published in English on May 10, 2013, as WO 2013/064681 A1), which claims priority under 35 U.S.C. §119 to U.S. Provisional Application No. 61/555,583, filed Nov. 4, 2011, and French Patent Application No. 1159997, filed Nov. 4, 2011. The contents of each hare hereby expressly incorporated by reference in its entirety and each assigned to the assignee thereof.

TECHNICAL FIELD

The present invention relates generally to the field of pharmaceuticals and cosmetics. More specifically, the present invention pertains to certain N-(pyrid-4-yl)amides and N-(pyrimidin-4-yl)amides, as described herein, which are potent modulators (e.g., inhibitors) of an androgen receptor, and which are useful, for example, in therapy, for example, in the treatment of a dermatological disease or disorder; a disease or disorder of the sebaceous gland(s); acne; hyperseborrhoea; oily skin; seborrhoeic dermatitis; hyperpilosity or hirsutism; atopic dermatitis; or androgenic alopecia; especially acne. The present invention also relates to compositions (e.g., pharmaceutical compositions, cosmetic compositions) comprising the compounds; methods of preparing the compositions; methods of modulating (e.g., inhibiting) an androgen receptor using the compounds and/or compositions; and medical and/or cosmetic use of the compounds and compositions.

BACKGROUND

A number of patents and publications are cited herein in order to describe and disclose the invention more fully and the state of the art to which the invention pertains. Each of these references is incorporated herein by reference in its entirety into the present disclosure, to the same extent as if each individual reference was specifically and individually indicated to be incorporated by reference.

Throughout this specification, including the claims that follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

The present invention relates to the provision of new amides that are potent modulators of androgen receptors.

Documents describing known modulators of androgen receptors include EP 0 079 191; WO 2010/143803; CN 1597662; WO 2004/064747; and WO 2005/000794.

SUMMARY OF THE INVENTION

One aspect of the present invention pertains to certain N-(pyrid-4-yl)amides and N-(pyrimidin-4-yl)amides, and pharmaceutically acceptable salts, hydrates, and solvates thereof, as described herein.

Another aspect of the present invention pertains to a composition (e.g., a pharmaceutical composition; a physiologically acceptable composition; a cosmetic composition) comprising an N-(pyrid-4-yl)amide or N-(pyrimidin-4-yl)amide, as described herein, and a carrier, diluent, or excipient (e.g., a pharmaceutically acceptable carrier, diluent, or excipient; a physiologically acceptable carrier, diluent, or excipient; a cosmetic carrier, diluent, or excipient).

Another aspect of the present invention pertains to a method of preparing a composition (e.g., a pharmaceutical composition; a physiologically acceptable composition; a cosmetic composition) comprising mixing an N-(pyrid-4-yl)amide or N-(pyrimidin-4-yl)amide, as described herein, and a carrier, diluent, or excipient (e.g., a pharmaceutically acceptable carrier, diluent, or excipient; a physiologically acceptable carrier, diluent, or excipient; a cosmetic carrier, diluent, or excipient).

Another aspect of the present invention pertains to a method of modulating (e.g., inhibiting) an androgen receptor, in vitro or in vivo, comprising contacting the androgen receptor with an effective amount of an N-(pyrid-4-yl)amide or N-(pyrimidin-4-yl)amide, as described herein.

Another aspect of the present invention pertains to a method of modulating (e.g., inhibiting) an androgen receptor in a cell, in vitro or in vivo, comprising contacting the cell with an effective amount of an N-(pyrid-4-yl)amide or N-(pyrimidin-4-yl)amide, as described herein.

Another aspect of the invention is an N-(pyrid-4-yl)amide or N-(pyrimidin-4-yl)amide as described herein for use in a method of treatment of the human or animal body.

Another aspect of the invention is an N-(pyrid-4-yl)amide or N-(pyrimidin-4-yl)amide as described herein for use in a method of treatment of a disease or disorder.

Another aspect of the invention is use of an N-(pyrid-4-yl)amide or N-(pyrimidin-4-yl)amide as described herein in the manufacture of a medicament for the treatment of a disease or disorder.

Another aspect of the invention is a method of treatment of a disease or disorder comprising administering a therapeutically-effective amount of an N-(pyrid-4-yl)amide or N-(pyrimidin-4-yl)amide as described herein to a patient in need of said treatment.

In one embodiment, the treatment is treatment of a disease or disorder that is ameliorated by the modulation (e.g., inhibition) of an androgen receptor.

In one embodiment, the treatment is treatment of an androgen-dependent disease or disorder.

In one embodiment, the treatment is treatment of a dermatological disease or disorder; a disease or disorder of the sebaceous gland(s); acne; hyperseborrhoea; oily skin; seborrhoeic dermatitis; hyperpilosity or hirsutism; atopic dermatitis; or androgenic alopecia.

In one embodiment, the treatment is treatment of acne.

Another aspect of the invention pertains to a kit comprising (a) an N-(pyrid-4-yl)amide or N-(pyrimidin-4-yl)amide as described herein, or a composition (e.g., a pharmaceutical composition; a physiologically acceptable composition; a cosmetic composition) comprising an N-(pyrid-4-yl)amide or N-(pyrimidin-4-yl)amide as described herein, e.g., preferably provided in a suitable container and/or with suitable packaging; and (b) instructions for use, e.g., written instructions on how to administer the compound or composition.

Another aspect of the present invention pertains to a physiologically acceptable composition (e.g., a cosmetic composition) comprising an N-(pyrid-4-yl)amide or N-(pyrimidin-4-yl)amide, as described herein, for use in a non-therapeutic method (e.g., a cosmetic method) of body care and/or hair care.

Another aspect of the present invention pertains to a non-therapeutic method (e.g., a cosmetic method) of body care and/or hair care, comprising applying to the body and/or hair of a subject an effective amount of an N-(pyrid-4-yl)amide or N-(pyrimidin-4-yl)amide, as described herein, preferably in the form of a physiologically acceptable composition (e.g., a cosmetic composition).

Another aspect of the present invention pertains to use of an N-(pyrid-4-yl)amide or N-(pyrimidin-4-yl)amide, as described herein, in a non-therapeutic method (e.g., a cosmetic method) of body care and/or hair care.

Another aspect of the present invention pertains to an N-(pyrid-4-yl)amide or N-(pyrimidin-4-yl)amide, as described herein, for use in a non-therapeutic method (e.g., a cosmetic method) of body care and/or hair care.

Another aspect of the present invention pertains to use of an N-(pyrid-4-yl)amide or N-(pyrimidin-4-yl)amide, as described herein, in the manufacture of physiologically acceptable composition (e.g., a cosmetic composition) for use in a non-therapeutic method of body care and/or hair care.

Another aspect of the present invention pertains to a non-therapeutic method (e.g., a cosmetic method) of body care and/or hair care, comprising applying to the body and/or hair of a subject an effective amount of a physiologically acceptable composition (e.g., a cosmetic composition) comprising an N-(pyrid-4-yl)amide or N-(pyrimidin-4-yl) amide, as described herein.

Another aspect of the present invention pertains to use of a physiologically acceptable composition (e.g., a cosmetic composition) comprising an N-(pyrid-4-yl)amide or N-(pyrimidin-4-yl)amide, as described herein in a non-therapeutic method (e.g., a cosmetic method) of body care and/or hair care.

Another aspect of the present invention pertains to a physiologically acceptable composition (e.g., a cosmetic composition) comprising an N-(pyrid-4-yl)amide or N-(pyrimidin-4-yl)amide, as described herein, for use in a non-therapeutic method (e.g., a cosmetic method) of body care and/or hair care.

Another aspect of the present invention is an N-(pyrid-4-yl)amide or N-(pyrimidin-4-yl)amide as described herein obtainable by a method of synthesis as described herein, or a method comprising a method of synthesis as described herein.

Another aspect of the present invention is an N-(pyrid-4-yl)amide or N-(pyrimidin-4-yl)amide as described herein obtained by a method of synthesis as described herein, or a method comprising a method of synthesis as described herein.

Another aspect of the present invention is a novel intermediate, as described herein, which is suitable for use in the methods of synthesis described herein.

Another aspect of the present invention is the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

The present invention relates to certain N-(pyrid-4-yl) amides and N-(pyrimidin-4-yl)amides which are structurally related to 2-hydroxy-N-(pyrid-4-yl)-acetamide and 2-hydroxy-N-(pyrimidin-4-yl)-acetamide.

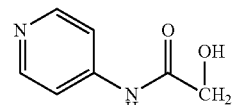

2-hydroxy-N-(pyrid-4-yl)-acetamide

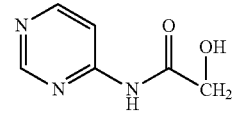

2-hydroxy-N-(pyrimidin-4-yl)-acetamide

Thus, one aspect of the present invention pertains to compounds of formula (1), and pharmaceutically acceptable salts, hydrates, and solvates thereof, wherein X, —$R^1$, —$R^2$, —$R^3$, and —$R^4$ are as defined herein:

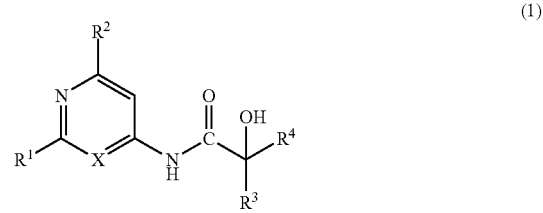

(1)

In one embodiment:

$R^1$ is $C_{1-6}$ alkyl, $C_{3-7}$ cycloalkyl, $C_{1-6}$ alkyloxy, —S(O)$_m$—$C_{1-6}$ alkyl, $C_{1-6}$ fluoroalkyl, $C_{1-6}$ fluoroalkyloxy, $C_{1-6}$ alkyl-OH, —(CH$_2$)$_i$—$C_{1-6}$ alkyloxy, —(CH$_2$)$_j$—O—$C_{1-6}$ fluoroalkyl, COR$^a$, CN, NO$_2$, NR$^5$R$^6$, or a halogen atom;

$R^2$ is a hydrogen atom, $C_{1-6}$ alkyl, $C_{3-7}$ cycloalkyl, $C_{1-6}$ alkyloxy, —S(O)$_n$—$C_{1-6}$ alkyl, $C_{1-6}$ fluoroalkyl, $C_{1-6}$ fluoroalkyloxy, $C_{1-6}$ alkyl-OH, —(CH$_2$)$_k$—$C_{1-6}$ alkyloxy, —(CH$_2$)$_l$—O—$C_{1-6}$ fluoroalkyl, COR$^b$, CN, NO$_2$, NR$^5$'R$^6$', OH, or a halogen atom;

$R^3$ and $R^4$ are identical or different and are a hydrogen atom, $C_{1-12}$ alkyl, $C_{3-9}$ cycloalkyl, $C_{1-6}$ fluoroalkyl, —C$_{1-6}$ alkyl-OH, —(CH$_2$)$_p$—C$_{1-6}$ alkyloxy, —(CH$_2$)$_q$—C$_{3-9}$ cycloalkyl, —(CH$_2$)$_r$—C$_{1-6}$ fluoroalkyl, —(CH$_2$)$_s$—O—C$_{1-6}$ fluoroalkyl, phenyl, heteroaryl, heterocyclyl group, —(CH$_2$)$_t$-phenyl, or —(CH$_2$)$_v$-heteroaryl, wherein each phenyl and heteroaryl is optionally substituted with one to three identical or different R$^c$ groups;

and additionally, R$^3$ and R$^4$, together with the carbon atom carrying them, may form a C$_{3-9}$ cycloalkyl group or a heterocyclyl group, such as tetrahydrofuranyl, tetrahydropyranyl, tetrahydrothiopyranyl, tetrahydro-1-oxo-thiopyranyl, or tetrahydro-1,1-dioxo-thiopyranyl;

R$^c$ is C$_{1-6}$ alkyl, C$_{3-7}$ cycloalkyl, C$_{1-6}$ alkyloxy, —S(O)$_u$—C$_{1-6}$ alkyl, C$_{1-6}$ fluoroalkyl, C$_{1-6}$ fluoroalkyloxy, C$_{1-6}$ alkyl-OH, COR$^d$, CN, NO$_2$, NR$^9$R$^{10}$, OH, or a halogen atom;

R$^a$, R$^b$, and R$^d$ are identical or different and are C$_{1-6}$ alkyl, C$_{1-6}$ alkyloxy, or NR$^7$R$^8$;

R$^5$, R$^{5'}$, R$^6$, R$^{6'}$, R$^7$, R$^8$, R$^9$ and R$^{10}$ are identical or different and are a hydrogen atom, C$_{1-6}$ alkyl, C$_{3-7}$ cycloalkyl, or —(CH$_2$)$_w$—C$_{3-7}$ cycloalkyl;

and additionally, R$_5$ and R$_6$, together with the nitrogen atom carrying them, may form a heterocyclyl group, such as: azetidinyl, pyrolidinyl, piperidinyl, azepanyl, morpholinyl, or piperazinyl;

and additionally, R$_{5'}$ and R$_{6'}$, together with the nitrogen atom carrying them, may form a heterocyclyl group, such as: azetidinyl, pyrolidinyl, piperidinyl azepanyl, morpholinyl, or piperazinyl;

and additionally, R$_7$ and R$_8$, together with the nitrogen atom carrying them, may form a heterocyclyl group, such as: azetidinyl, pyrolidinyl, piperidinyl, azepanyl, morpholinyl, or piperazinyl;

and additionally, R$_9$ and R$_{10}$, together with the nitrogen atom carrying them, may form a heterocyclyl group, such as: azetidinyl, pyrolidinyl, piperidinyl, azepanyl, morpholinyl, or piperazinyl;

i, j, k, l, p, q, r, s, t, v, and w are different or identical and are 1, 2 or 3;

m, n, and u are different or identical and are 0, 1 or 2; and

X is CH or N.

Depending upon the values of R$^3$ and R$^4$, the carbon atom to which they are attached may be chiral, and if so, may independently be in the (R) or (S) configuration. Unless otherwise indicated, it is intended that both configurations are encompassed. In one embodiment, the configuration is (S). In one embodiment, the configuration is (R).

The following is understood in the context of the invention:

C$_{b-c}$, where b and c may assume values from 1 to 12, is a carbon chain of b to c carbon atoms, for example C$_{1-6}$, being a carbon chain that may have 1 to 6 carbon atoms.

alkyl is a linear or branched saturated aliphatic group, for example a C$_{1-6}$ alkyl group is a linear or branched carbon chain of 1 to 6 atom atoms, for example, methyl, ethyl, propyl, isopropyl, butyl, isobutyl, sec-butyl, tert-butyl, pentyl, isopentyl, hexyl, and isohexyl.

cycloalkyl is a cyclic, possibly branched, saturated carbon chain comprising 3 to 7 carbon atoms, and a C$_{3-7}$ cycloalkyl group is a carbon chain of 3 to 7 carbon atoms, for example, cyclopropyl, cyclobutyl, cyclopentyl, cyclohexyl, and cycloheptyl.

heterocyclyl is a cyclic or bicyclic, saturated or unsaturated hydrocarbon chain comprising one or more heteroatoms selected from O, S and N, including examples such as azetidinyl, pyrolidinyl, piperidinyl azepanyl, morpholinyl, piperazinyl, tetrahydrofuranyl, tetrahydropyranyl, and morpholinyl.

heteroaryl is an aromatic heterocyclyl group, for example, pyridinyl, pyrazinyl, pyrimidinyl, pyridazinyl, triazinyl, pyrazolyl, oxazolyl, isoxazolyl, thiazolyl, isothiazolyl, oxadiazolyl, thiadiazolyl, triazolyl, and imidazolyl.

halogen is a fluorine, chlorine, or bromine atom.

alkyloxy is an —O-alkyl group.

fluoroalkyl is an alkyl group wherein one or more hydrogen atoms has/have been replaced by a fluorine atom, for example, —CF$_3$.

fluoroalkyloxy is an alkyloxy group wherein one or more hydrogen atoms has/have been replaced by a fluorine atom, for example, —OCF$_3$.

In some preferred embodiments:

R$^1$ is a halogen atom, methyl, ethyl, isopropyl, trifluoromethyl, nitrile, nitro, methoxy, ethoxy, isopropoxy, thiomethyl, thioethyl, thio isopropyl, or methyl sulphone; and/or R$^2$ is a hydrogen atom, a halogen atom, methyl, ethyl, isopropyl, trifluoromethyl, nitrile, nitro, methoxy, ethoxy, isopropoxy, thiomethyl, thioethyl, or thio isopropyl; and/or, R$^3$ and R$^4$ are identical or different and are a hydrogen atom, C$_{1-12}$ alkyl, C$_{3-9}$ cycloalkyl, —(CH$_2$)$_q$—C$_{3-9}$ cycloalkyl, phenyl, heteroaryl, a heterocyclyl group, —(CH$_2$)$_t$-phenyl, or —(CH$_2$)$_v$-heteroaryl, wherein each phenyl and heteroaryl is optionally substituted with one to three identical or different R$^c$ groups.

In some more preferred embodiments:

R$^1$ is a halogen atom, methyl, ethyl, methoxy, ethoxy, thiomethyl, thioethyl, trifluoromethyl, nitrile, or methyl sulphone; and/or, R$^2$ is a hydrogen atom, a chlorine atom, a bromine atom, methyl, ethyl, methoxy, ethoxy, thiomethyl, thioethyl, or trifluoromethyl; and/or, R$^3$ and R$^4$ are identical or different and are a hydrogen atom, C$_{1-12}$ alkyl, C$_{3-9}$ cycloalkyl, —(CH$_2$)$_q$—C$_{3-9}$ cycloalkyl, phenyl, heteroaryl, a heterocyclyl group, —(CH$_2$)$_t$-phenyl, or —(CH$_2$)$_v$-heteroaryl, wherein each phenyl and heteroaryl is optionally substituted with one to three identical or different R$^c$ groups.

The Group X

In one embodiment, X is CH or N.

In one embodiment, X is CH.

In one embodiment, X is N.

The Group R$^1$

In one embodiment, R$^1$ is C$_{1-6}$ alkyl, C$_{3-7}$ cycloalkyl, C$_{1-6}$ alkyloxy, —S(O)$_m$—C$_{1-6}$ alkyl, C$_{1-6}$ fluoroalkyl, C$_{1-6}$ fluoroalkyloxy, C$_{1-6}$ alkyl-OH, —(CH$_2$)$_j$—C$_{1-6}$ alkyloxy, —(CH$_2$)$_j$—O—C$_{1-6}$ fluoroalkyl, COR$^a$, CN, NO$_2$, NR$_5$R$_6$, or a halogen atom.

In one embodiment, R$^1$ is a halogen atom, methyl, ethyl, isopropyl, trifluoromethyl, nitrile, nitro, methoxy, ethoxy, isopropoxy, thiomethyl, thioethyl, thio isopropyl, or methyl sulphone.

In one embodiment, R$^1$ is a halogen atom, methyl, ethyl, methoxy, ethoxy, thiomethyl, thioethyl, trifluoromethyl, nitrile, or methyl sulphone.

In one embodiment, R$^1$ is a halogen atom, methyl, ethyl, methoxy, ethoxy, trifluoromethyl, or nitrile.

In one embodiment, R$^1$ is a bromine atom or methoxy.

In one embodiment, R$^1$ is a bromine atom.

In one embodiment, R$^1$ is methoxy.

The Group $R^2$

In one embodiment, $R^2$ is a hydrogen atom, $C_{1-6}$ alkyl, $C_{3-7}$ cycloalkyl, $C_{1-6}$ alkyloxy, —S(O)$_n$—$C_{1-6}$ alkyl, $C_{1-6}$ fluoroalkyl, $C_{1-6}$ fluoroalkyloxy, $C_{1-6}$ alkyl-OH, —(CH$_2$)$_k$—$C_{1-6}$ alkyloxy, —(CH$_2$)$_l$—O—$C_{1-6}$ fluoroalkyl, COR$^b$, CN, NO$_2$, NR$^5$'R$^{6'}$, OH, or a halogen atom.

In one embodiment, $R^2$ is a hydrogen atom, a halogen atom, methyl, ethyl, isopropyl, trifluoromethyl, nitrile, nitro, methoxy, ethoxy, isopropoxy, thiomethyl, thioethyl, or thio isopropyl.

In one embodiment, $R^2$ is a hydrogen atom, a chlorine atom, a bromine atom, methyl, ethyl, methoxy, ethoxy, thiomethyl, thioethyl, or trifluoromethyl.

In one embodiment, $R^2$ is a hydrogen atom, methyl, or methoxy.

In one embodiment, $R^2$ is a hydrogen atom or methoxy.

In one embodiment, $R^2$ is a hydrogen atom.

In one embodiment, $R^2$ is methoxy.

The Groups $R^3$ and $R^4$

In one embodiment, $R^3$ and $R^4$ are identical or different and are a hydrogen atom, $C_{1-12}$ alkyl, $C_{3-9}$ cycloalkyl, $C_{1-6}$ fluoroalkyl, —$C_{1-6}$ alkyl-OH, —(CH$_2$)$_p$—$C_{1-6}$ alkyloxy, —(CH$_2$)$_q$—$C_{3-9}$ cycloalkyl, —(CH$_2$)$_r$—$C_{1-6}$ fluoroalkyl, —(CH$_2$)$_s$—O—$C_{1-6}$ fluoroalkyl, phenyl, heteroaryl, heterocyclyl, —(CH$_2$)$_t$-phenyl, or —(CH$_2$)$_v$-heteroaryl, wherein each phenyl and heteroaryl is optionally substituted with one to three identical or different R$^c$ groups; and additionally, R$_3$ and R$_4$, together with the carbon atom carrying them, may form a $C_{3-9}$ cycloalkyl group or a heterocyclyl group, such as tetrahydrofuranyl, tetrahydropyranyl, tetrahydrothiopyranyl, tetrahydro-1-oxo-thiopyranyl, or tetrahydro-1,1-dioxothiopyranyl.

In one embodiment, $R^3$ and $R^4$ are identical or different and are a hydrogen atom, $C_{1-12}$ alkyl, $C_{3-9}$ cycloalkyl, $C_{1-6}$ fluoroalkyl, —$C_{1-6}$ alkyl-OH, —(CH$_2$)$_p$—$C_{1-6}$ alkyloxy, —(CH$_2$)$_q$—$C_{3-9}$ cycloalkyl, —(CH$_2$)$_r$—$C_{1-6}$ fluoroalkyl, —(CH$_2$)$_s$—O—$C_{1-6}$ fluoroalkyl, phenyl, heteroaryl, heterocyclyl, —(CH$_2$)$_t$-phenyl, or —(CH$_2$)$_v$-heteroaryl, wherein each phenyl and heteroaryl is optionally substituted with one to three identical or different R$^c$ groups; and additionally, R$_3$ and R$_4$, together with the carbon atom carrying them, may form a $C_{3-9}$ cycloalkyl group.

In one embodiment, $R^3$ and $R^4$ are identical or different and are a hydrogen atom, $C_{1-12}$ alkyl, $C_{3-9}$ cycloalkyl, —(CH$_2$)$_q$—$C_{3-9}$ cycloalkyl, phenyl, heteroaryl, a heterocyclyl group, —(CH$_2$)$_t$-phenyl, or —(CH$_2$)$_v$-heteroaryl, wherein each phenyl and heteroaryl is optionally substituted with one to three identical or different R$^c$ groups.

In one embodiment, $R^3$ and $R^4$, together with the carbon atom carrying them, form a $C_{3-9}$ cycloalkyl group.

In one embodiment, $R^3$ and $R^4$, together with the carbon atom carrying them, form a cyclopentyl group or a cyclohexyl group.

The Group $R^3$

In one embodiment, $R^3$ is a hydrogen atom, $C_{1-12}$ alkyl, $C_{3-9}$ cycloalkyl, —(CH$_2$)$_q$—$C_{3-9}$ cycloalkyl, phenyl, heteroaryl, heterocyclyl, —(CH$_2$)$_t$-phenyl, or —(CH$_2$)$_v$-heteroaryl, wherein each phenyl and heteroaryl is optionally substituted with one to three identical or different R$^c$ groups.

In one embodiment, $R^3$ is a hydrogen atom, $C_{1-8}$ alkyl, $C_{3-7}$ cycloalkyl, —(CH$_2$)$_q$—$C_{3-7}$ cycloalkyl, phenyl, heteroaryl, heterocyclyl, —(CH$_2$)$_t$-phenyl, or —(CH$_2$)$_v$-heteroaryl, wherein each phenyl and heteroaryl is optionally substituted with one to three identical or different R$^c$ groups.

In one embodiment, $R^3$ is a hydrogen atom, $C_{1-12}$ alkyl, $C_{3-9}$ cycloalkyl, or phenyl, wherein phenyl is optionally substituted with one to three identical or different R$^c$ groups.

In one embodiment, $R^3$ is a hydrogen atom, $C_{1-8}$ alkyl, $C_{3-7}$ cycloalkyl, or phenyl, wherein phenyl is optionally substituted with one to three identical or different R$^c$ groups.

In one embodiment, $R^3$ is $C_{1-8}$ alkyl, $C_{3-7}$ cycloalkyl, or phenyl, wherein phenyl is optionally substituted with one to three identical or different R$^c$ groups.

In one embodiment, $R^3$ is a hydrogen atom, $C_{1-8}$ alkyl, $C_{3-7}$ cycloalkyl, or phenyl.

In one embodiment, $R^3$ is $C_{1-8}$ alkyl, $C_{3-7}$ cycloalkyl, or phenyl.

In one embodiment, $R^3$ is a hydrogen atom.

In one embodiment, $R^3$ is $C_{1-8}$ alkyl.

In one embodiment, $R^3$ is methyl, ethyl, propyl, isopropyl, butyl, isobutyl, sec-butyl, tert-butyl, pentyl, isopentyl, hexyl, isohexyl, heptyl, or isoheptyl.

In one embodiment, $R^3$ is methyl, ethyl, propyl, isopropyl, butyl, isobutyl, sec-butyl, or tert-butyl.

In one embodiment, $R^3$ is methyl, ethyl, propyl, isopropyl, butyl, or isobutyl.

In one embodiment, $R^3$ is methyl, ethyl, propyl, or isopropyl.

In one embodiment, $R^3$ is methyl or ethyl.

In one embodiment, $R^3$ is methyl.

In one embodiment, $R^3$ is $C_{3-7}$ cycloalkyl.

In one embodiment, $R^3$ is cyclopropyl, cyclobutyl, cyclopentyl, or cyclohexyl.

In one embodiment, $R^3$ is cyclopropyl, cyclobutyl, or cyclopentyl.

In one embodiment, $R^3$ is phenyl optionally substituted with one to three identical or different R$^c$ groups.

In one embodiment, $R^3$ is phenyl.

The Group $R^4$

In one embodiment, $R^4$ is $C_{1-12}$ alkyl, $C_{3-9}$ cycloalkyl, —$C_{1-6}$ alkyl-OH, —(CH$_2$)$_p$—$C_{1-6}$ alkyloxy, —(CH$_2$)$_q$—$C_{3-9}$ cycloalkyl, phenyl, or —(CH$_2$)$_t$-phenyl, wherein each phenyl is optionally substituted with one to three identical or different R$^c$ groups.

In one embodiment, $R^4$ is $C_{1-8}$ alkyl, $C_{3-7}$ cycloalkyl, —$C_{1-6}$ alkyl-OH, —(CH$_2$)$_p$—$C_{1-6}$ alkyloxy, —(CH$_2$)$_q$—$C_{3-7}$ cycloalkyl, phenyl, or —(CH$_2$)$_t$-phenyl, wherein each phenyl is optionally substituted with one to three identical or different R$^c$ groups.

In one embodiment, $R^4$ is $C_{1-8}$ alkyl, $C_{3-7}$ cycloalkyl, —$C_{1-6}$ alkyl-OH, or —(CH$_2$)$_t$-phenyl, wherein phenyl is optionally substituted with one to three identical or different R$^c$ groups.

In one embodiment, $R^4$ is $C_{1-8}$ alkyl.

In one embodiment, $R^4$ is methyl, ethyl, propyl, isopropyl, butyl, isobutyl, sec-butyl, tert-butyl, pentyl, isopentyl, hexyl, isohexyl, heptyl, or isoheptyl.

In one embodiment, $R^4$ is $C_{3-8}$ alkyl.

In one embodiment, $R^4$ is propyl, isopropyl, butyl, isobutyl, sec-butyl, tert-butyl, pentyl, isopentyl, hexyl, isohexyl, heptyl, or isoheptyl.

In one embodiment, $R^4$ is propyl, isopropyl, butyl, isobutyl, sec-butyl, tert-butyl, pentyl, isopentyl, hexyl, or isohexyl.

In one embodiment, $R^4$ is propyl, isopropyl, butyl, isobutyl, sec-butyl, tert-butyl, pentyl, or isopentyl.

In one embodiment, $R^4$ is propyl or isopropyl.

In one embodiment, $R^4$ is butyl, isobutyl, sec-butyl, or tert-butyl.

In one embodiment, $R^4$ is butyl or isobutyl.

In one embodiment, $R^4$ is isobutyl.

In one embodiment, $R^4$ is pentyl or isopentyl.

In one embodiment, $R^4$ isopentyl.

In one embodiment, $R^4$ is $C_{3-7}$ cycloalkyl.

In one embodiment, $R^4$ is cyclopropyl, cyclobutyl, cyclopentyl, or cyclohexyl.

In one embodiment, $R^4$ is cyclopropyl, cyclobutyl, or cyclopentyl.

In one embodiment, $R^4$ is phenyl, wherein phenyl is optionally substituted with one to three identical or different $R^c$ groups.

The Groups $R^a$, $R^b$, and $R^d$

The groups $R^a$, $R^b$, and $R^d$ appear in the groups $COR^a$, $COR^b$, and $COR^d$.

In one embodiment, $R^a$, $R^b$, and $R^d$, if present, are identical or different and are $C_{1-6}$ alkyl, $C_{1-6}$ alkyloxy, or $NR^7R^8$.

In one embodiment, $R^a$, if present, is $C_{1-6}$ alkyl.
In one embodiment, $R^a$, if present, is $C_{1-6}$ alkyloxy.
In one embodiment, $R^a$, if present, is $NR^7R^8$.
In one embodiment, $R^b$, if present, is $C_{1-6}$ alkyl.
In one embodiment, $R^b$, if present, is $C_{1-6}$ alkyloxy.
In one embodiment, $R^b$, if present, is $NR^7R^8$.
In one embodiment, $R^d$, if present, is $C_{1-6}$ alkyl.
In one embodiment, $R^d$, if present, is $C_{1-6}$ alkyloxy.
In one embodiment, $R^d$, if present, is $NR^7R^8$.

The Group $R^c$

The group $R^c$ appears as an optional substituent on phenyl and heteroaryl.

In one embodiment, each $R^c$, if present, is identical or different and is $C_{1-6}$ alkyl, $C_{3-7}$ cycloalkyl, $C_{1-6}$ alkyloxy, $-S(O)_u-C_{1-6}$ alkyl, $C_{1-6}$ fluoroalkyl, $C_{1-6}$ fluoroalkyloxy, $C_{1-6}$ alkyl-OH, $COR^d$, CN, $NO_2$, $NR^9R^{10}$, OH, or a halogen atom.

In one embodiment, each $R^c$, if present, is identical or different and is $C_{1-6}$ alkyl, $C_{1-6}$ alkyloxy, $-S(O)_u-C_{1-6}$ alkyl, $C_{1-6}$ fluoroalkyl, $C_{1-6}$ fluoroalkyloxy, $C_{1-6}$ alkyl-OH, $COR^d$, $NR^9R^{10}$, OH, or a halogen atom.

In one embodiment, each $R^c$, if present, is identical or different and is $C_{1-6}$ alkyl, $C_{1-6}$ alkyloxy, $C_{1-6}$ fluoroalkyl, $C_{1-6}$ fluoroalkyloxy, OH, or a halogen atom.

In one embodiment, each $R^c$, if present, is identical or different and is $C_{1-6}$ alkyl, $C_{1-6}$ alkyloxy, OH, or a halogen atom.

In one embodiment, each $R^c$, if present, is identical or different and is methyl, ethyl, propyl, isopropyl, butyl, isobutyl, sec-butyl, tert-butyl, methoxy, ethoxy, propoxy, isopropoxy, butoxy, isobutoxy, sec-butoxy, tert-butoxy, OH, a fluorine atom, a chlorine atom, or a bromine atom.

In one embodiment, each $R^c$, if present, is identical or different and is methyl, ethyl, methoxy, ethoxy, propoxy, OH, a fluorine atom, a chlorine atom, or a bromine atom.

The Groups $R^5$, $R^{5'}$, $R^6$, $R^{6'}$, $R^7$, $R^8$, $R^9$ and $R^{10}$

The groups $R^5$, $R^{5'}$, $R^6$, $R^{6'}$, $R^7$, $R^8$, $R^9$ and $R^{10}$ appear in the groups $NR^5R^6$, $NR^{5'}R^{6'}$, $NR^7R^8$, and $NR^9R^{10}$.

In one embodiment, $R^5$, $R^{5'}$, $R^6$, $R^{6'}$, $R^7$, $R^8$, $R^9$ and $R^{10}$, if present, are identical or different and are a hydrogen atom, $C_{1-6}$ alkyl, $C_{3-7}$ cycloalkyl, or $-(CH_2)_w-C_{3-7}$ cycloalkyl;

and additionally, $R^5$ and $R^6$, together with the nitrogen atom carrying them, may form a heterocyclyl group;

and additionally, $R^{5'}$ and $R^{6'}$, together with the nitrogen atom carrying them, may form a heterocyclyl group;

and additionally, $R^7$ and $R^8$, together with the nitrogen atom carrying them, may form a heterocyclyl group;

and additionally, $R^9$ and $R^{10}$, together with the nitrogen atom carrying them, may form a heterocyclyl group.

In one embodiment, $R^5$, $R^{5'}$, $R^6$, $R^{6'}$, $R^7$, $R^8$, $R^9$ and $R^{10}$, if present, are identical or different and are a hydrogen atom, $C_{1-6}$ alkyl, $C_{3-7}$ cycloalkyl, or $-(CH_2)_w-C_{3-7}$ cycloalkyl;

and additionally, $R^5$ and $R^6$, together with the nitrogen atom carrying them, may form azetidinyl, pyrolidinyl, piperidinyl, azepanyl, morpholinyl, or piperazinyl;

and additionally, $R^{5'}$ and $R^{6'}$, together with the nitrogen atom carrying them, may form azetidinyl, pyrolidinyl, piperidinyl azepanyl, morpholinyl, or piperazinyl;

and additionally, $R^7$ and $R^8$, together with the nitrogen atom carrying them, may form azetidinyl, pyrolidinyl, piperidinyl, azepanyl, morpholinyl, or piperazinyl;

and additionally, $R^9$ and $R^{10}$, together with the nitrogen atom carrying them, may form azetidinyl, pyrolidinyl, piperidinyl, azepanyl, morpholinyl, or piperazinyl.

The Indices i, j, k, l, p, q, r, s, t, v, and w

The indices i, j, k, l, p, q, r, s, t, v, and w appear in the groups $-(CH_2)_i-$, $-(CH_2)_j-$, $-(CH_2)_k-$, $-(CH_2)_l-$, $-(CH_2)_p-$, $-(CH_2)_q-$, $-(CH_2)_r-$, $-(CH_2)_s-$, $-(CH_2)_t-$, $-(CH_2)_v-$, and $-(CH_2)_w-$.

In one embodiment, i, j, k, l, p, q, r, s, t, v, and w, if present, are different or identical and are 1, 2 or 3.

In one embodiment, i, j, k, l, p, q, r, s, t, v, and w, if present, are different or identical and are 1 or 2.

In one embodiment, i, if present, is 1.
In one embodiment, i, if present, is 2.
In one embodiment, i, if present, is 3.
In one embodiment, j, if present, is 1.
In one embodiment, j, if present, is 2.
In one embodiment, j, if present, is 3.
In one embodiment, k, if present, is 1.
In one embodiment, k, if present, is 2.
In one embodiment, k, if present, is 3.
In one embodiment, l, if present, is 1.
In one embodiment, l, if present, is 2.
In one embodiment, l, if present, is 3.
In one embodiment, p, if present, is 1.
In one embodiment, p, if present, is 2.
In one embodiment, p, if present, is 3.
In one embodiment, q, if present, is 1.
In one embodiment, q, if present, is 2.
In one embodiment, q, if present, is 3.
In one embodiment, r, if present, is 1.
In one embodiment, r, if present, is 2.
In one embodiment, r, if present, is 3.
In one embodiment, s, if present, is 1.
In one embodiment, s, if present, is 2.
In one embodiment, s, if present, is 3.
In one embodiment, t, if present, is 1.
In one embodiment, t, if present, is 2.
In one embodiment, t, if present, is 3.
In one embodiment, v, if present, is 1.
In one embodiment, v, if present, is 2.
In one embodiment, v, if present, is 3.
In one embodiment, w, if present, is 1.
In one embodiment, w, if present, is 2.
In one embodiment, w, if present, is 3.

The Indices m, n, and u

The indices m, n, and u appear in the groups $-S(O)_m-$, $-S(O)_n-$, and $-S(O)_u-$.

In one embodiment, m, if present, is 0.
In one embodiment, m, if present, is 1.
In one embodiment, m, if present, is 2.
In one embodiment, n, if present, is 0.
In one embodiment, n, if present, is 1.
In one embodiment, n, if present, is 2.
In one embodiment, u, if present, is 0.
In one embodiment, u, if present, is 1.
In one embodiment, u, if present, is 2.

Configuration

If $R^3$ and $R^4$ are different, then the carbon atom to which $R^3$ and $R^4$ are attached is chiral, and may be in the (S) configuration or the (R) configuration.

In one embodiment, if $R^3$ and $R^4$ are different, then the carbon atom to which $R^3$ and $R^4$ are attached is in the (S) configuration.

In one embodiment, if $R^3$ and $R^4$ are different, then the carbon atom to which $R^3$ and $R^4$ are attached is in the (R) configuration.

Specific Compounds

In one embodiment, the compound is a compound selected from the following compounds, or a pharmaceutically acceptable salt, hydrate, or solvate thereof:

| Compound No. | Name | Structure |
| --- | --- | --- |
| 1 | 2-Hydroxy-2-methyl-pentanoic acid (2-bromo-pyridin-4-yl)-amide | 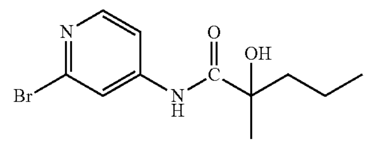 [SMILES: CCCC(C)(O)C(=O)Nc1ccnc(Br)c1] |
| 2 | 2-Ethyl-2-hydroxy-5-methyl-hexanoic acid (2-bromo-pyridin-4-yl)-amide | 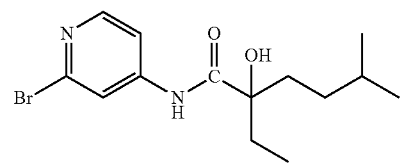 [SMILES: CCC(O)(CCC(C)C)C(=O)Nc1ccnc(Br)c1] |
| 3 | N-(2-Bromo-pyridin-4-yl)-2-hydroxy-2-(4-methoxy-phenyl)-propionamide | 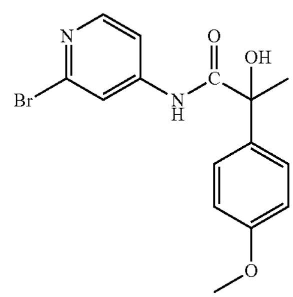 [SMILES: COc1ccc(C(C)(O)C(=O)Nc2ccnc(Br)c2)cc1] |
| 4 | 2-Hydroxy-2,4-dimethyl-pentanoic acid (2-bromo-pyridin-4-yl)-amide | 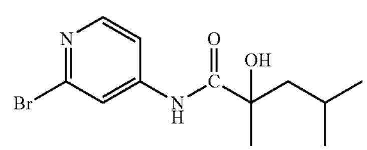 [SMILES: CC(C)CC(C)(O)C(=O)Nc1ccnc(Br)c1] |
| 5 | 2-Ethyl-2-hydroxy-hexanoic acid (2-bromo-6-methoxy-pyridin-4-yl)-amide | 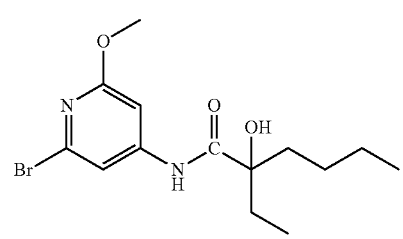 [SMILES: CCCCC(O)(CC)C(=O)Nc1cc(Br)nc(OC)c1] |
| 6 | 2-Hydroxy-2-propyl-pentanoic acid (2-bromo-pyridin-4-yl)-amide | 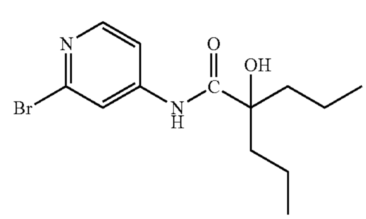 [SMILES: CCCC(O)(CCC)C(=O)Nc1ccnc(Br)c1] |

-continued

| Compound No. | Name | Structure |
|---|---|---|
| 7 | N-(2-Bromo-pyridin-4-yl)-2-cyclohexyl-2-hydroxy-butyramide | 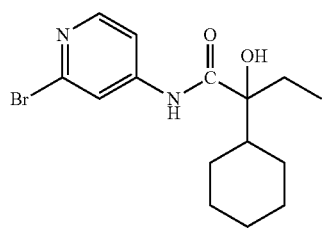 [SMILES: CCC(O)(C(=O)Nc1ccnc(Br)c1)C1CCCCC1] |
| 8 | 2-Hydroxy-2-methyl-hexanoic acid (2-bromo-6-methoxy-pyridin-4-yl)-amide | 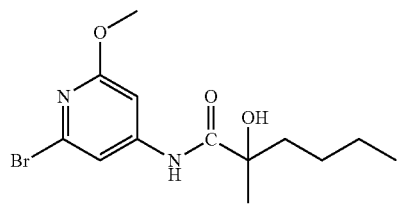 [SMILES: CCCCC(C)(O)C(=O)Nc1cc(Br)nc(OC)c1] |
| 9 | N-(2-Bromo-6-methoxy-pyridin-4-yl)-2-cyclopentyl-2-hydroxy-butyramide | 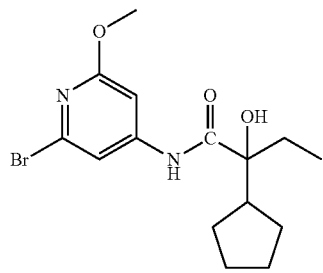 [SMILES: CCC(O)(C(=O)Nc1cc(Br)nc(OC)c1)C1CCCC1] |
| 10 | N-(2-Bromo-pyridin-4-yl)-2-hydroxy-2-(2-methoxy-phenyl)-propionamide | 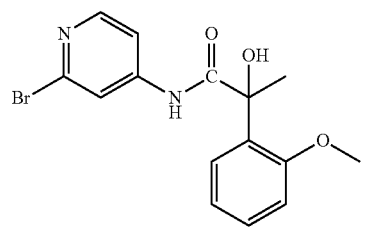 [SMILES: COc1ccccc1C(C)(O)C(=O)Nc1ccnc(Br)c1] |
| 11 | 2-Hydroxy-2-methyl-pentanoic acid (2,6-dimethoxy-pyrimidin-4-yl)-amide | 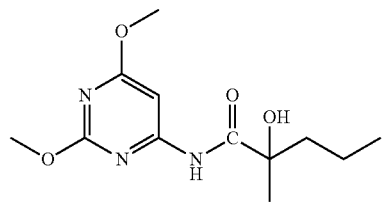 [SMILES: CCCC(C)(O)C(=O)Nc1cc(OC)nc(OC)n1] |
| 12 | 2-Hydroxy-2-methyl-octanoic acid (2-bromo-6-methoxy-pyridin-4-yl)-amide | 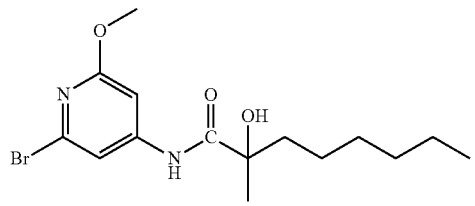 [SMILES: CCCCCCC(C)(O)C(=O)Nc1cc(Br)nc(OC)c1] |

-continued

| Compound No. | Name | Structure |
|---|---|---|
| 13 | N-(2-Bromo-6-methoxy-pyridin-4-yl)-2-ethyl-2-hydroxy-3-methyl-butyramide | 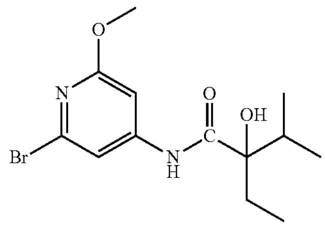 [SMILES: CCC(O)(C(=O)Nc1cc(Br)nc(OC)c1)C(C)C] |
| 14 | N-(2-Bromo-pyridin-4-yl)-2-hydroxy-2-methyl-propionamide | 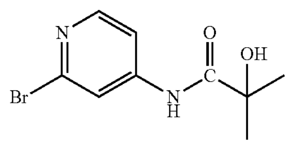 |
| 15 | N-(2-Bromo-pyridin-4-yl)-2-hydroxy-2-methyl-butyramide | 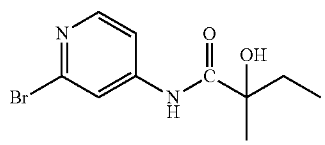 |
| 16 | 2-Ethyl-2-hydroxy-4-methyl-pentanoic acid (2-bromo-6-methoxy-pyridin-4-yl)-amide | 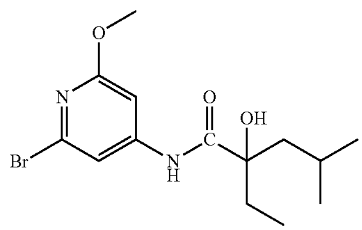 [SMILES: CCC(O)(CC(C)C)C(=O)Nc1cc(Br)nc(OC)c1] |
| 17 | N-(2-Bromo-pyridin-4-yl)-2-cyclopentyl-2-hydroxy-propionamide | 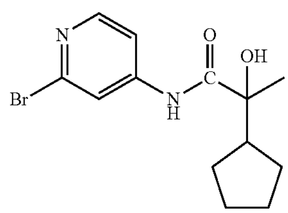 [SMILES: CC(O)(C(=O)Nc1ccnc(Br)c1)C1CCCC1] |
| 18 | 2-Hydroxy-2-methyl-heptanoic acid (2-bromo-6-methoxy-pyridin-4-yl)-amide | 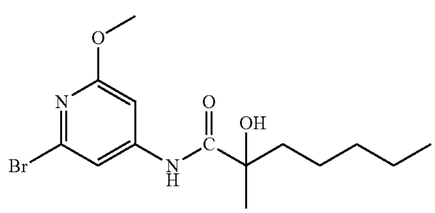 [SMILES: CCCCCC(C)(O)C(=O)Nc1cc(Br)nc(OC)c1] |
| 19 | 2-Ethyl-2-hydroxy-pentanoic acid (2-bromo-6-methoxy-pyridin-4-yl)-amide | 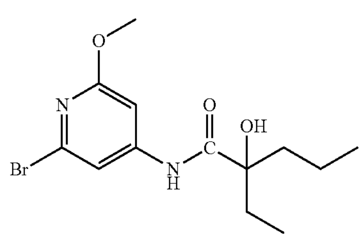 [SMILES: CCCC(O)(CC)C(=O)Nc1cc(Br)nc(OC)c1] |
| 20 | 2-Hydroxy-2,4-dimethyl-pentanoic acid (2-methoxy-pyridin-4-yl)-amide | 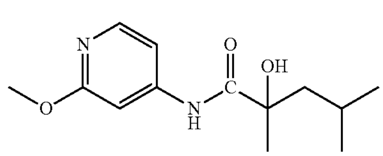 [SMILES: COc1cc(NC(=O)C(C)(O)CC(C)C)ccn1] |

| Compound No. | Name | Structure |
|---|---|---|
| 21 | N-(2-Bromo-6-methoxy-pyridin-4-yl)-2-cyclopentyl-2-hydroxy-propionamide | 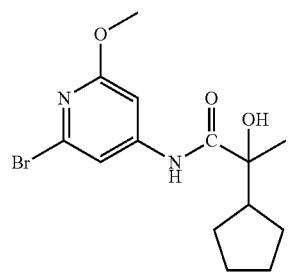 [SMILES: COc1cc(NC(=O)C(C)(O)C2CCCC2)cc(Br)n1] |
| 22 | N-(2-Bromo-6-methoxy-pyridin-4-yl)-2-ethyl-2-hydroxy-butyramide | 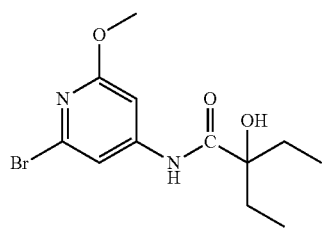 |
| 23 | 2-Butyl-2-hydroxy-hexanoic acid (2-bromo-pyridin-4-yl)-amide | 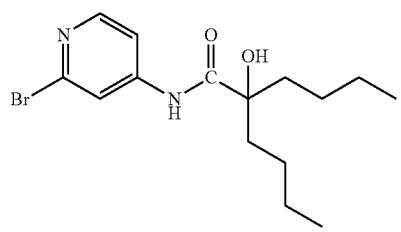 [SMILES: CCCCC(O)(CCCC)C(=O)Nc1ccnc(Br)c1] |
| 24 | N-(2-Bromo-pyridin-4-yl)-2-hydroxy-4-(4-methoxy-phenyl)-2-methyl-butyramide | 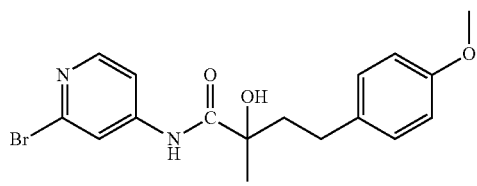 [SMILES: COc1ccc(CCC(C)(O)C(=O)Nc2ccnc(Br)c2)cc1] |
| 25 | N-(2-Bromo-6-methoxy-pyridin-4-yl)-2-hydroxy-2,3-dimethyl-butyramide | 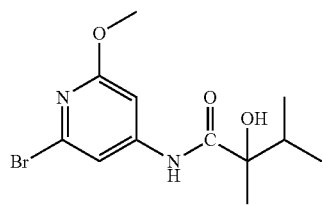 |
| 26 | N-(2-Bromo-6-methoxy-pyridin-4-yl)-2-hydroxy-2-methyl-4-phenyl-butyramide | 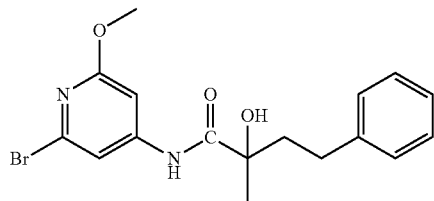 [SMILES: COc1cc(NC(=O)C(C)(O)CCc2ccccc2)cc(Br)n1] |

-continued

| Compound No. | Name | Structure |
|---|---|---|
| 27 | 2-(4-Fluoro-phenyl)-2-hydroxy-N-(2-methoxy-pyridin-4-yl)-propionamide | 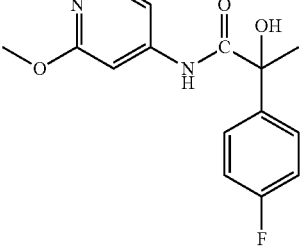 |
| 28 | N-(2-Bromo-pyridin-4-yl)-2-hydroxy-4-(2-methoxy-phenyl)-2-methyl-butyramide | 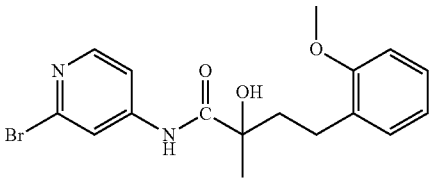 [SMILES: COc1ccccc1CCC(C)(O)C(=O)Nc1ccnc(Br)c1] |
| 29 | 2-Hydroxy-2-propyl-pentanoic acid (2-bromo-6-methoxy-pyridin-4-yl)-amide | 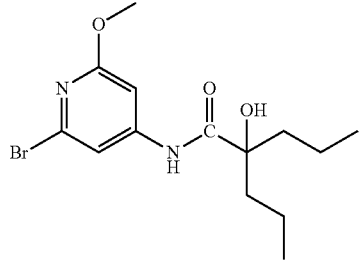 [SMILES: CCCC(O)(CCC)C(=O)Nc1cc(Br)nc(OC)c1] |
| 30 | 3-(4-Fluoro-phenyl)-2-hydroxy-N-(2-methoxy-pyridin-4-yl)-2-methyl-propionamide | 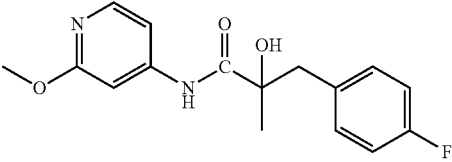 [SMILES: COc1cc(NC(=O)C(C)(O)Cc2ccc(F)cc2)ccn1] |
| 31 | N-(2-Bromo-pyridin-4-yl)-2-ethyl-2-hydroxy-butyramide | 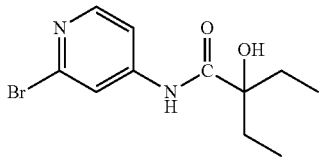 |
| 32 | N-(2-Bromo-pyridin-4-yl)-2-hydroxy-2-phenyl-propionamide | 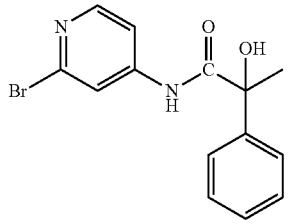 [SMILES: CC(O)(C(=O)Nc1ccnc(Br)c1)c1ccccc1] |
| 33 | N-(2-Bromo-pyridin-4-yl)-2-hydroxy-2-methyl-3-phenyl-propionamide | 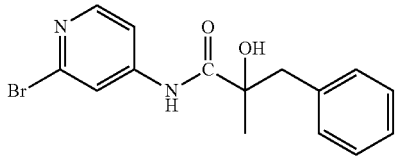 [SMILES: CC(O)(Cc1ccccc1)C(=O)Nc1ccnc(Br)c1] |

-continued

| Compound No. | Name | Structure |
|---|---|---|
| 34 | 2-Hydroxy-2-methyl-heptanoic acid (2-bromo-pyridin-4-yl)-amide | 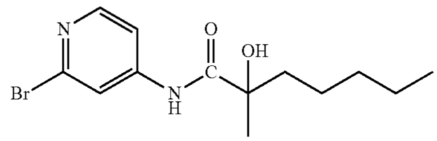 [SMILES: CCCCCC(C)(O)C(=O)Nc1ccnc(Br)c1] |
| 35 | N-(2-Bromo-pyridin-4-yl)-2-hydroxy-2-(3-methoxy-phenyl)-propionamide | 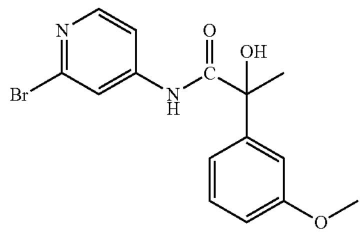 [SMILES: COc1cccc(C(C)(O)C(=O)Nc2ccnc(Br)c2)c1] |
| 36 | 2-Ethyl-2-hydroxy-pentanoic acid (2-methoxy-pyridin-4-yl)-amide | 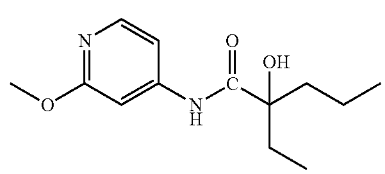 [SMILES: CCCC(O)(CC)C(=O)Nc1ccnc(OC)c1] |
| 37 | N-(2-Bromo-pyridin-4-yl)-2-hydroxy-4-(3-methoxy-phenyl)-2-methyl-butyramide | 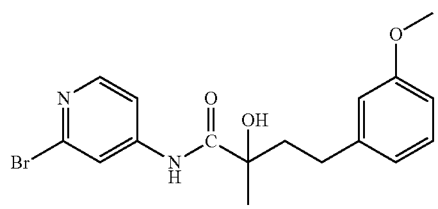 [SMILES: COc1cccc(CCC(C)(O)C(=O)Nc2ccnc(Br)c2)c1] |
| 38 | N-(2-Bromo-6-methoxy-pyridin-4-yl)-2-hydroxy-2-methyl-propionamide | 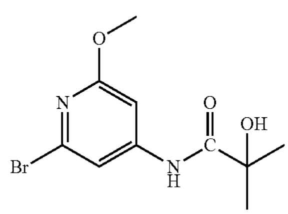 [SMILES: COc1cc(NC(=O)C(C)(C)O)cc(Br)n1] |
| 39 | 2-Hydroxy-2-methyl-pentanoic acid (2-methoxy-pyridin-4-yl)-amide | 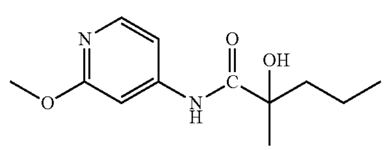 [SMILES: CCCC(C)(O)C(=O)Nc1ccnc(OC)c1] |
| 40 | 2-Hydroxy-2-methyl-octanoic acid (2-bromo-pyridin-4-yl)-amide | 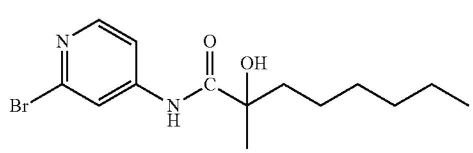 [SMILES: CCCCCCC(C)(O)C(=O)Nc1ccnc(Br)c1] |
| 41 | 2-Hydroxy-2,4-dimethyl-pentanoic acid (2-bromo-6-methoxy-pyridin-4-yl)-amide | 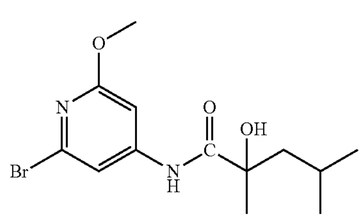 [SMILES: COc1cc(NC(=O)C(C)(O)CC(C)C)cc(Br)n1] |

-continued

| Compound No. | Name | Structure |
|---|---|---|
| 42 | 2-Hydroxy-2-methyl-hexanoic acid (2-bromo-6-methyl-pyridin-4-yl)-amide | 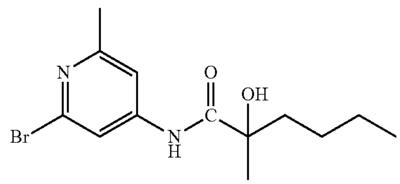 [SMILES: CCCCC(C)(O)C(=O)Nc1cc(C)nc(Br)c1] |
| 43 | N-(2-Bromo-pyridin-4-yl)-2-hydroxy-2-methyl-4-phenyl-butyramide | 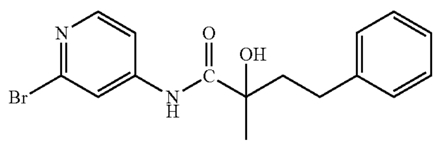 [SMILES: CC(O)(CCc1ccccc1)C(=O)Nc1ccnc(Br)c1] |
| 44 | N-(2-Bromo-6-methoxy-pyridin-4-yl)-2-hydroxy-2-phenyl-propionamide | 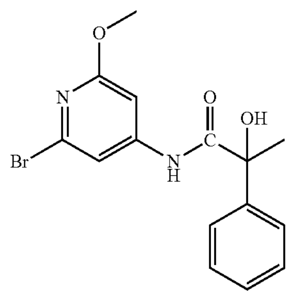 [SMILES: COc1cc(NC(=O)C(C)(O)c2ccccc2)cc(Br)n1] |
| 45 | 2-Hydroxy-2-methyl-hexanoic acid (2-bromo-pyridin-4-yl)-amide | 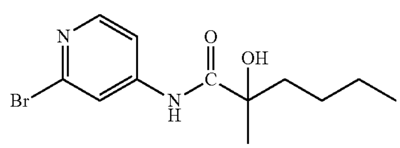 [SMILES: CCCCC(C)(O)C(=O)Nc1ccnc(Br)c1] |
| 46 | 2-Ethyl-2-hydroxy-pentanoic acid (2-bromo-pyridin-4-yl)-amide | 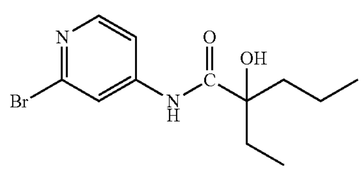 [SMILES: CCCC(O)(CC)C(=O)Nc1ccnc(Br)c1] |
| 47 | N-(2-Bromo-pyridin-4-yl)-2-(4-fluoro-phenyl)-2-hydroxy-butyramide | 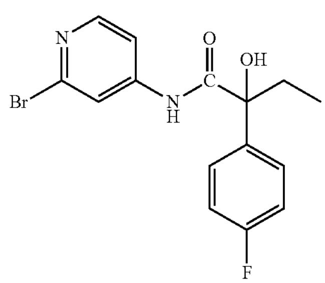 [SMILES: CCC(O)(C(=O)Nc1ccnc(Br)c1)c1ccc(F)cc1] |
| 48 | 2-Ethyl-2-hydroxy-4-methyl-pentanoic acid (2-bromo-pyridin-4-yl)-amide | 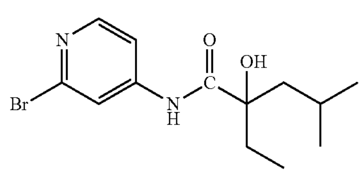 [SMILES: CCC(O)(CC(C)C)C(=O)Nc1ccnc(Br)c1] |

-continued

| Compound No. | Name | Structure |
|---|---|---|
| 49 | 2-Ethyl-2-hydroxy-hexanoic acid (2-bromo-pyridin-4-yl)-amide | 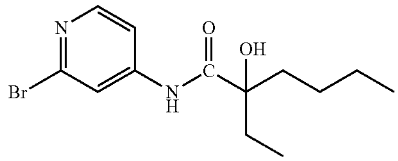 [SMILES: CCCCC(O)(CC)C(=O)Nc1ccnc(Br)c1] |
| 50 | 2-Hydroxy-2-methyl-pentanoic acid (2-trifluoromethyl-pyridin-4-yl)-amide | 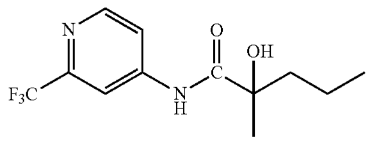 [SMILES: CCCC(C)(O)C(=O)Nc1ccnc(C(F)(F)F)c1] |
| 51 | N-(2-Bromo-pyridin-4-yl)-2-cyclopentyl-2-hydroxy-butyramide | 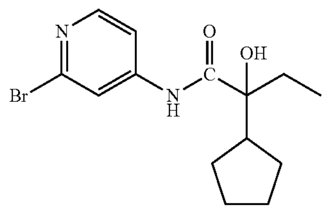 [SMILES: CCC(O)(C(=O)Nc1ccnc(Br)c1)C1CCCC1] |
| 52 | 2-Ethyl-2,6-dihydroxy-hexanoic acid (2-bromo-pyridin-4-yl)-amide | 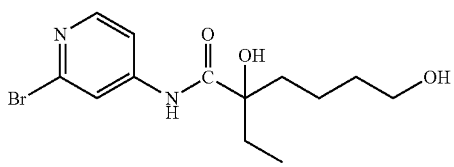 [SMILES: CCC(O)(CCCCO)C(=O)Nc1ccnc(Br)c1] |
| 53 | 2-Hydroxy-2,4-dimethyl-pentanoic acid (2-cyano-6-methoxy-pyridin-4-yl)-amide | 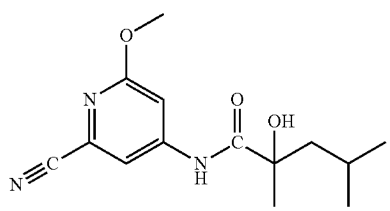 [SMILES: COc1cc(NC(=O)C(C)(O)CC(C)C)cc(C#N)n1] |
| 54 | N-(2-Bromo-6-methoxy-pyridin-4-yl)-2-hydroxy-propionamide | 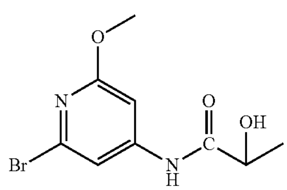 |
| 55 | N-(2-Bromo-6-methoxy-pyridin-4-yl)-2-hydroxy-butyramide | 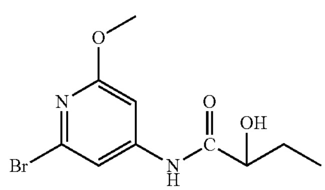 [SMILES: CCC(O)C(=O)Nc1cc(Br)nc(OC)c1] |
| 56 | N-(2-Bromo-6-methoxy-pyrimidin-4-yl)-2-ethyl-2-hydroxy-butyramide | 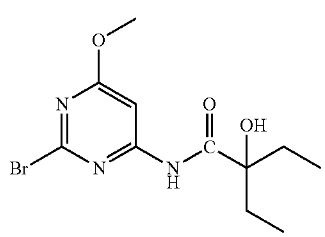 [SMILES: CCC(O)(CC)C(=O)Nc1cc(OC)nc(Br)n1] |

-continued

| Compound No. | Name | Structure |
|---|---|---|
| 57 | 1-Hydroxy-cyclopentanecarboxylic acid (2-bromo-pyridin-4-yl)-amide | 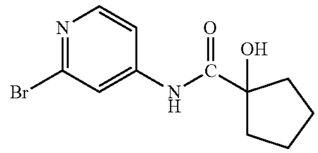 [SMILES: O=C(Nc1ccnc(Br)c1)C1(O)CCCC1] |
| 58 | 1-Hydroxy-cyclohexanecarboxylic acid (2-bromo-pyridin-4-yl)-amide | 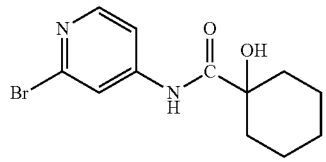 [SMILES: O=C(Nc1ccnc(Br)c1)C1(O)CCCCC1] |
| 59 | 4-(2-Hydroxy-2-methyl-pentanoylamino)-pyridine-2-carboxylic acid methyl ester | 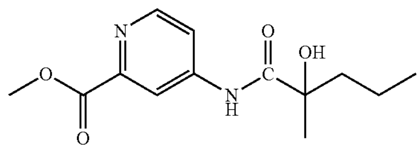 [SMILES: CCCC(C)(O)C(=O)Nc1ccnc(C(=O)OC)c1] |
| 60 | 2-Hydroxy-2-methyl-pentanoic acid (2-bromo-6-methoxy-pyridin-4-yl)-amide | 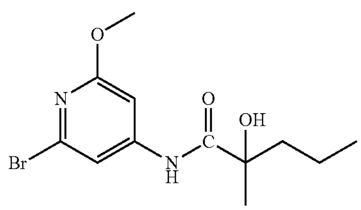 [SMILES: CCCC(C)(O)C(=O)Nc1cc(Br)nc(OC)c1] |
| 61 | 2-Hydroxy-2-methyl-pentanoic acid (6-bromo-2-oxo-1,2-dihydro-pyridin-4-yl)-amide (see note below) | 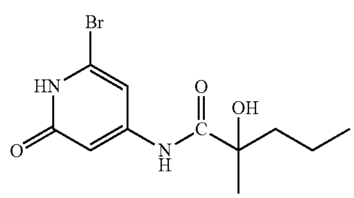 [SMILES: CCCC(C)(O)C(=O)Nc1cc(Br)[nH]c(=O)c1] |
| 62 | N-(2-Bromo-6-methoxy-pyridin-4-yl)-2-hydroxy-2-methyl-butyramide | 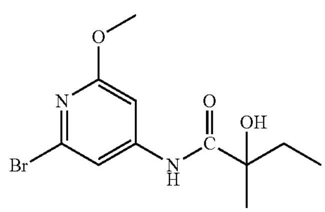 [SMILES: CCC(C)(O)C(=O)Nc1cc(Br)nc(OC)c1] |
| 63 | 2-Hydroxy-hexanoic acid (2-bromo-6-methoxy-pyridin-4-yl)-amide | 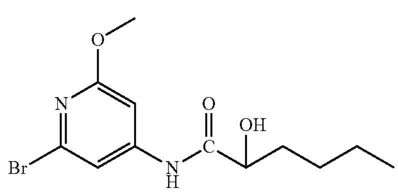 [SMILES: CCCCC(O)C(=O)Nc1cc(Br)nc(OC)c1] |
| 64 (and 65) | 2-Hydroxy-2-isopropyl-pentanoic acid (2-bromo-6-methoxy-pyridin-4-yl)-amide | 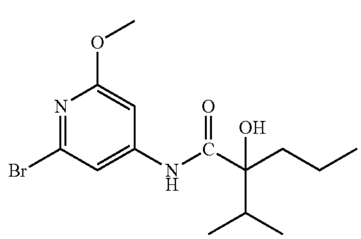 [SMILES: CCCC(O)(C(=O)Nc1cc(Br)nc(OC)c1)C(C)C] |

-continued

| Compound No. | Name | Structure |
|---|---|---|
| 66 | 2-Butyl-2-hydroxy-hexanoic acid (2-bromo-6-methoxy-pyridin-4-yl)-amide | 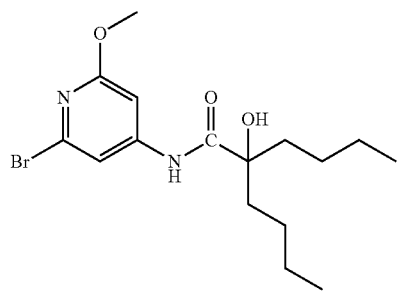 [SMILES: CCCCC(O)(CCCC)C(=O)Nc1cc(Br)nc(OC)c1] |
| 67 | N-(2-Bromo-6-methoxy-pyridin-4-yl)-2,2-dicyclopentyl-2-hydroxy-acetamide | 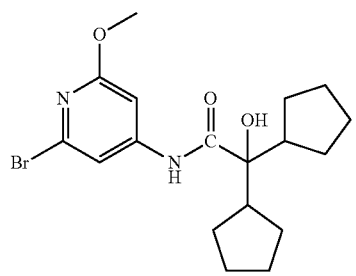 [SMILES: COc1cc(NC(=O)C(O)(C2CCCC2)C2CCCC2)cc(Br)n1] |
| 68 | N-(2-Bromo-6-methoxy-pyridin-4-yl)-2-hydroxy-2-isopropyl-3-methyl-butyramide | 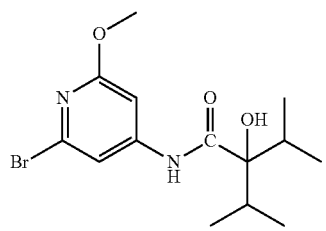 |
| 69 | N-(2-Bromo-6-methoxy-pyridin-4-yl)-2-hydroxy-2-(tetrahydro-pyran-4-yl)-propionamide | 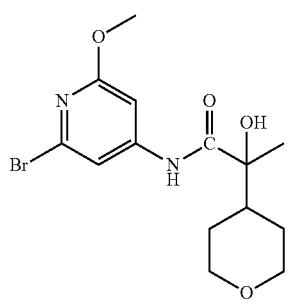 [SMILES: COc1cc(NC(=O)C(C)(O)C2CCOCC2)cc(Br)n1] |
| 70 | 2-Hydroxy-2-propyl-hexanoic acid (2-bromo-6-methoxy-pyridin-4-yl)-amide | 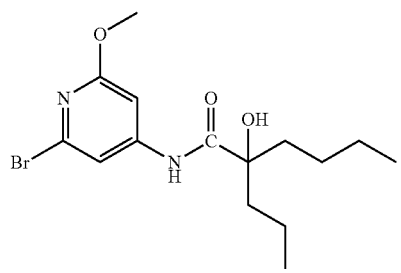 [SMILES: CCCCC(O)(CCC)C(=O)Nc1cc(Br)nc(OC)c1] |

Note:

Compound 61 is named and drawn above as a 1H-pyridin-2-one, that is, as the tautomer of 2-hydroxy-2-methyl-pentanoic acid (6-bromo-2-hydroxy-pyridin-4-yl)-amide. As discussed below, and unless otherwise specified, it is intended that a reference to one tautomer encompasses all tautomers.

In one embodiment, the compound is a compound selected from the following compounds, or a pharmaceutically acceptable salt, hydrate, or solvate thereof:

| Compound No. | Name | Structure |
|---|---|---|
| 81 | N-(2-Bromo-6-methoxy-pyridin-4-yl)-2-cyclopropyl-2-hydroxy-propionamide | 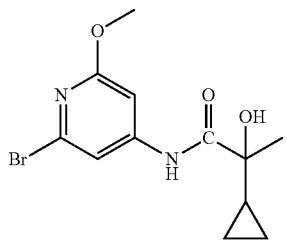 [SMILES: COc1cc(NC(=O)C(C)(O)C2CC2)cc(Br)n1] |
| 82 | N-(2-Bromo-6-methoxy-pyridin-4-yl)-2-cyclopropyl-2-hydroxy-butyramide | 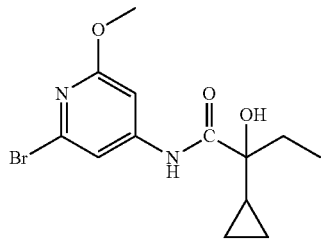 [SMILES: CCC(O)(C(=O)Nc1cc(Br)nc(OC)c1)C1CC1] |
| 83 | N-(2-Bromo-6-methoxy-pyridin-4-yl)-2-cyclobutyl-2-hydroxy-butyramide | 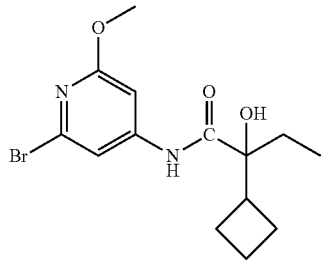 [SMILES: CCC(O)(C(=O)Nc1cc(Br)nc(OC)c1)C1CCC1] |
| 84 | N-(2-Bromo-6-methoxy-pyridin-4-yl)-2,2-dicyclopropyl-2-hydroxy-acetamide | 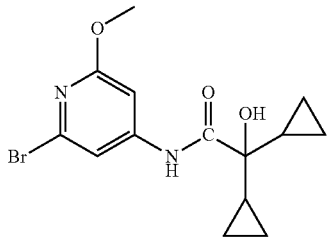 [SMILES: COc1cc(NC(=O)C(O)(C2CC2)C2CC2)cc(Br)n1] |
| 85 | N-(2-Bromo-6-methoxy-pyridin-4-yl)-2,2-dicyclobutyl-2-hydroxy-acetamide | 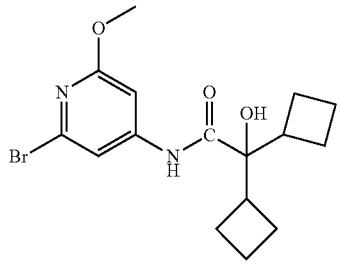 [SMILES: COc1cc(NC(=O)C(O)(C2CCC2)C2CCC2)cc(Br)n1] |

-continued

| Compound No. | Name | Structure |
|---|---|---|
| 86 | 2-Cyclopropyl-2-hydroxy-pentanoic acid (2-bromo-6-methoxy-pyridin-4-yl)-amide | 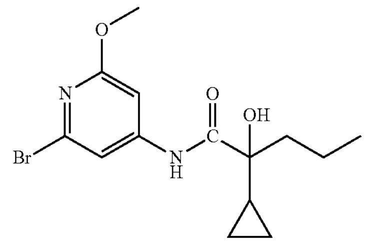 [SMILES: CCCC(O)(C(=O)Nc1cc(Br)nc(OC)c1)C1CC1] |
| 87 | 2-Cyclopropyl-2-hydroxy-4-methyl-pentanoic acid (2-bromo-6-methoxy-pyridin-4-yl)-amide | 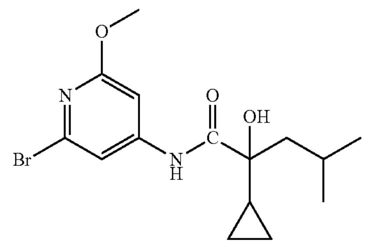 [SMILES: COc1cc(NC(=O)C(O)(CC(C)C)C2CC2)cc(Br)n1] |
| 88 | 2-Cyclobutyl-2-hydroxy-4-methyl-pentanoic acid (2-bromo-6-methoxy-pyridin-4-yl)-amide | 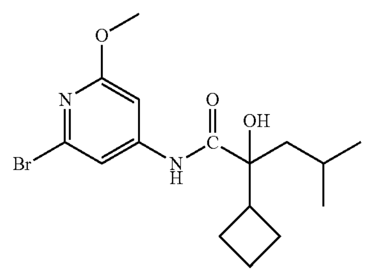 [SMILES: COc1cc(NC(=O)C(O)(CC(C)C)C2CCC2)cc(Br)n1] |
| 89 | 2-Hydroxy-2,4-dimethyl-pentanoic acid (2,6-dimethoxy-pyridin-4-yl)-amide | 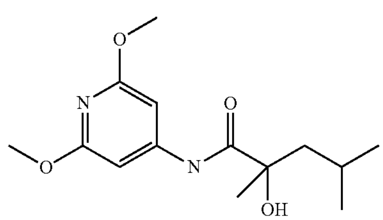 [SMILES: COc1cc(NC(=O)C(C)(O)CC(C)C)cc(OC)n1] |

In one embodiment, the compound is the following compound, or a pharmaceutically acceptable salt, hydrate, or solvate thereof:

| Compound No. | Name | Structure |
|---|---|---|
| 41 | 2-Hydroxy-2,4-dimethyl-pentanoic acid (2-bromo-6-methoxy-pyridin-4-yl)-amide | 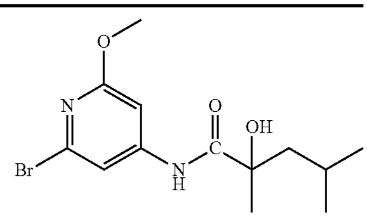 |

In one embodiment, the compound is the following compound, or a pharmaceutically acceptable salt, hydrate, or solvate thereof:

| Compound No. | Name | Structure |
|---|---|---|
| 71A | (R)-2-Hydroxy-2,4-dimethyl-pentanoic acid (2-bromo-6-methoxy-pyridin-4-yl)-amide | 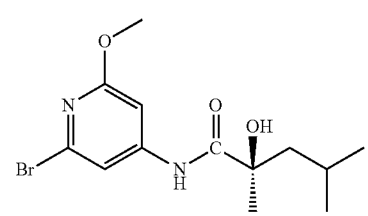 |

In one embodiment, the compound is the following compound, or a pharmaceutically acceptable salt, hydrate, or solvate thereof:

| Compound No. | Name | Structure |
|---|---|---|
| 71B | (S)-2-Hydroxy-2,4-dimethyl-pentanoic acid (2-bromo-6-methoxy-pyridin-4-yl)-amide | 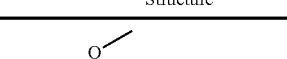 |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., $R^1$, $R^2$, $R^3$, $R^4$, $R^5$, $R^{5'}$, $R^6$, $R^{6'}$, $R^7$, $R^8$, $R^9$, $R^{10}$, $R^a$, $R^b$, $R^c$, $R^d$, X, i, j, k, l, m, n, p, q, r, s, t, u, v, w, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to certain N-(pyrid-4-yl)amides and N-(pyrimidin-4-yl)amides, as described herein, in substantially purified form and/or in a form substantially free from contaminants.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and 3-forms; axial and equatorial forms; boat-, chair-, twist-, envelope-, and halfchair-forms; and combinations thereof, hereinafter collectively referred to as "isomers" (or "isomeric forms").

For example, the N-(pyrid-4-yl)amides and N-(pyrimidin-4-yl)amides described herein may have one or more chiral carbon atoms. Such compounds may therefore exist in the form of a particular enantiomer or disastereoisomer, or a mixture of enantiomers or diastereoisomers. These enantiomers and diastereoisomers, as well as their mixtures, including the racemic mixtures, form part of the invention.

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-8}$alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

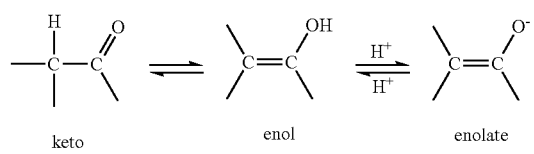

For example, 1H-pyridin-2-one and 2-hydroxy-pyridine are tautomers (as shown below).

For example, Compound 61 is named and drawn above as a 1H-pyridin-2-one, that is, as the tautomer of 2-hydroxy-2-methyl-pentanoic acid (6-bromo-2-hydroxy-pyridin-4-yl)-amide. Unless otherwise specified, it is intended that a reference to one tautomer encompasses all tautomers.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

For example, the N-(pyrid-4-yl)amides and N-(pyrimidin-4-yl)amides described herein may exist in the base state or state of addition salts with acids. Such addition salts form part of the invention. These salts may be advantageously prepared with pharmaceutically acceptable acids, but the salts of other useful acids, for example those used for the purification or isolation of the compounds may also be used, and also form part of the invention. These acids may be, for example, hydrochloric acid or nitric acid. For a review of physiologically acceptable salts see the Handbook of Pharmaceutical Salts: Properties, Selection and Use by Stahl and Wermuth (Wiley-VCH, 2002).

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a hemi-hydrate, a mono-hydrate, a di-hydrate, a tri-hydrate, etc.

For example, the solvates and/or hydrates may be obtained directly at the end of the synthesis process, with the target compound being isolated in the form of a hydrate, for example a mono- or hemi-hydrate, or in the form of a solvate of the reaction solvent and/or purification solvent.

Unless otherwise specified, a reference to a particular compound also includes solvate (e.g., hydrate) forms thereof.

Typical procedures for making and identifying suitable hydrates and solvates are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999.

Hydrates and solvates can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis.

For the avoidance of doubt, it is understood that the phrase "pharmaceutically acceptable salts and solvates thereof" and the phrase "pharmaceutically acceptable salt or solvate thereof" embrace pharmaceutically acceptable solvates (e.g., hydrates) of the compounds, pharmaceutically acceptable salts of the compounds, as well as pharmaceutically acceptable solvates (e.g., hydrates) of pharmaceutically acceptable salts of the compounds.

Chemical Synthesis

Methods for the chemical synthesis of the N-(pyrid-4-yl) amides and N-(pyrimidin-4-yl)amides (as described herein) are described herein. These and/or other well-known methods may be modified and/or adapted in known ways in order to facilitate the synthesis of additional N-(pyrid-4-yl)amides and N-(pyrimidin-4-yl)amides (as described herein).

Compounds of formula (1) may be prepared, for example, by the methods described in Scheme 1 and Scheme 2 below.
Scheme 1
Method 1a
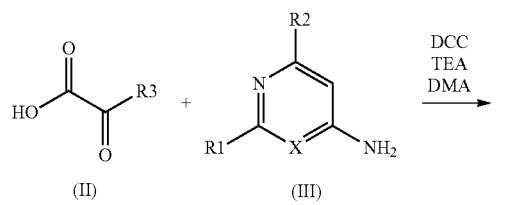
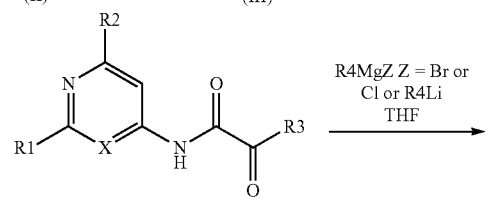
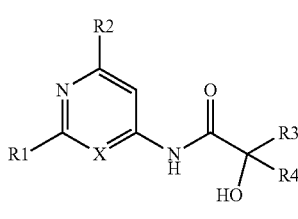
Method 1b
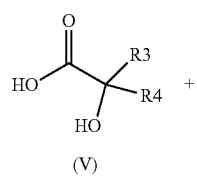
-continued
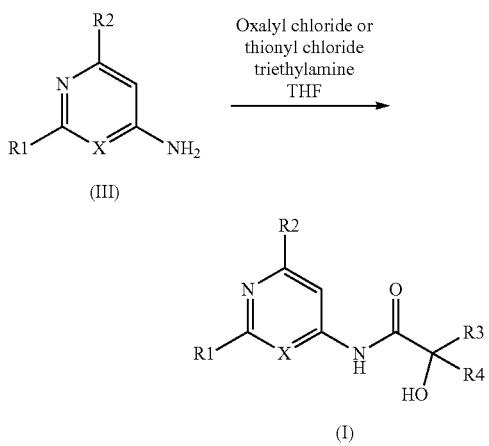
Method 1c
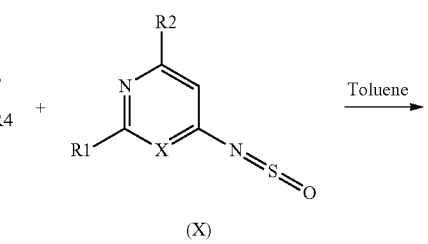
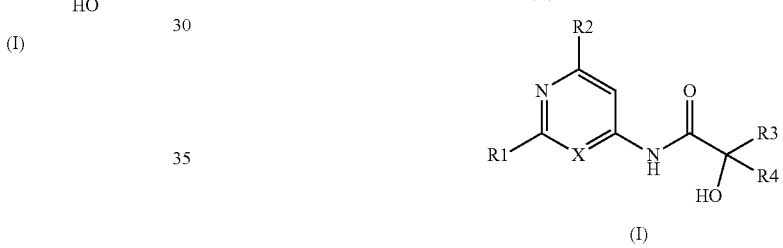
Scheme 2
Method 1d
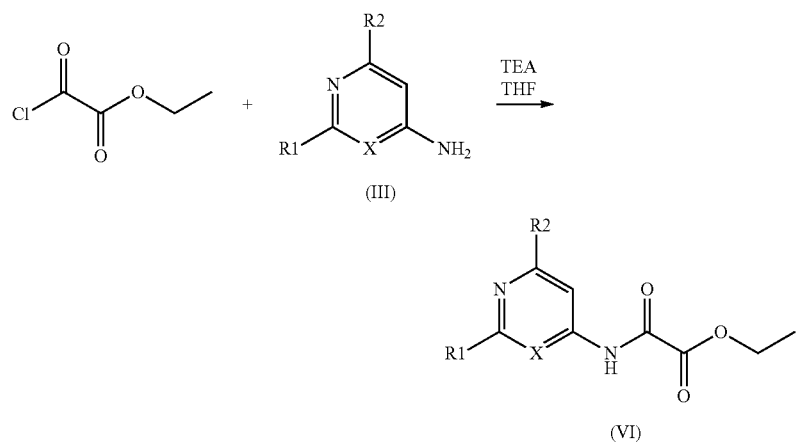

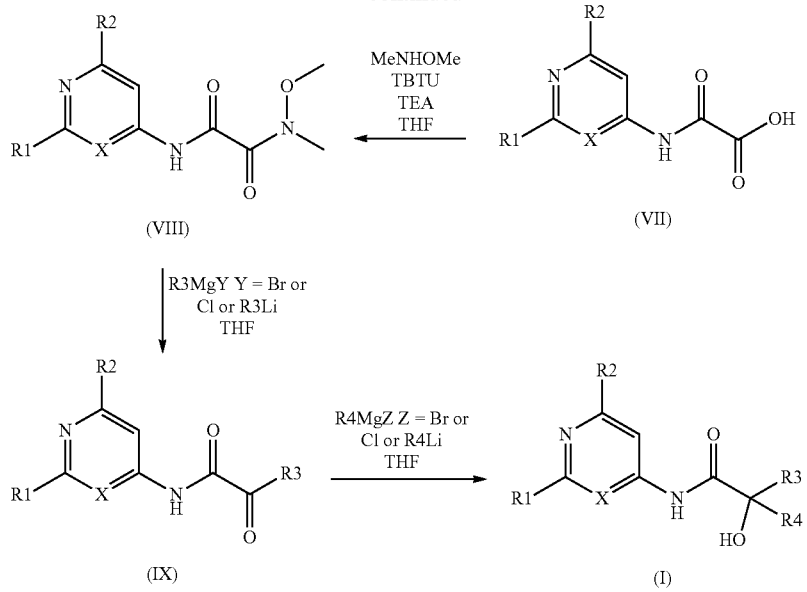

In one approach, compounds of formula (1) may be prepared from an intermediate of the ketoamide type of formula (IV), by reaction with an organometallic derivative such as an organomagnesium compound (R4MgY) or an organolithium compound (R4Li) in a solvent such as, for example, tetrahydrofuran, according to Method 1a illustrated in Scheme 1.

The intermediaries of the ketoamide type of formula (IV) may be prepared by a peptidic coupling reaction between a ketoacid of formula (II) and an amine of formula (III) in the presence of a coupling agent, for example, but not limited to, dicyclohexylcarbodiimide by analogy, for example, to the reactions described in Bodansky, M., *Synthesis* (1972), pp. 453-463. Amines of formula (III) are commercially available and/or may be prepared according to methods well known to the person skilled in the art.

In another approach, compounds of formula (1) may be prepared by a reaction between an acid of formula (V), activated in the form of an acyl chloride by means, for example, of oxalyl chloride or thionyl chloride, and an amine of formula (III), in the presence of a base such as triethylamine and in a solvent such as tetrahydrofuran, for example, according to Method 1b illustrated in Scheme 1.

The acid compounds of formula (V) are commercially available and/or can be prepared, for example, from ketoacids of formula (II) by reaction with an organometallic derivative such as an organomagnesium compound (R4MgY) or an organolithium compound (R4Li) in a solvent such as, for example, tetrahydrofuran, according to Scheme 3. The ketoacids of formula (II) are commercially available compounds and/or may be prepared according to methods well known to the person skilled in the art.

Scheme 3

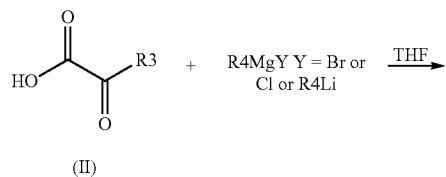

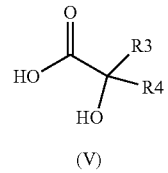

In another approach, compounds of formula (1) may be prepared by a reaction between an acid of formula (V) and a compound of the sulfinyl amine type of formula (X) in a solvent such as toluene, for example, according to Method 1c illustrated in Scheme 1 and by analogy, for example, to the reactions described in Hee Kim Yong et al., *Tetrahedron Letters*, (1985), pp. 3821-3824.

The compounds of the type sulfinyl amine of formula (X) may be prepared from amines of formula (III) by reaction, for example, with thionyl chloride, as described in Hee Kim Yong et al., *Tetrahedron Letters*, (1985), pp. 3821-3824 or Hanson et al., *J. Chem. Soc. Perkin Trans.* 1, (1990), pp. 2089-2097.

In another approach, compounds of formula (1) may also be prepared by the reaction of an organometallic derivative such as an organomagnesium compound (R4MgZ) or an organolithium compound (R4Li) and a ketoamide intermediate of formula (IV) according to Method 1d illustrated in Scheme 2 and by analogy, for example, with the reactions described in Grimm et al., *Bioorganic & Medicinal Chemistry*, (2003), pp. 4133-4141.

The ketoamide derivatives of formula (IX) may be prepared by the reaction of an intermediary N-methoxy N-methyl oxalamide, of formula (VIII) and an organometallic derivative such as an organomagnesium compound (R4MgZ) or an organolithium compound (R4Li) in a solvent such as tetrahydrofuran (THF), for example.

The intermediates N-methoxy N-methyl oxalamide of formula (VIII) may be prepared by peptidic coupling between an acid intermediary of formula (VII) and O,N-dimethylhydroxylamine in the presence of a coupling agent, for example, and not limited to, O-benzotriazolyl tetramethylisouronium tetrafluoroborate (TBTU), in the presence of a base such as triethyl amine (TEA), for example, in a solvent such as tetrahydrofuran, for example, and by analogy, for example, with the reactions described in Gillessen, D., *Tetrahedron Letters*, (1989) pp. 1927-1930.

The acid intermediates of formula (VII) may be obtained by hydrolysis of the intermediate of formula (VI), for example by means of aqueous sodium hydroxide.

The intermediates of formula (VI) may be obtained by peptidic coupling between amines of formula (III) and ethyl oxalate chloride in the presence of a base such as triethylamine, for example, in a solvent such as tetrahydrofuran, for example.

Compositions

Another aspect of the present invention pertains to a composition (e.g., a pharmaceutical composition; a physiologically acceptable composition; a cosmetic composition) comprising an N-(pyrid-4-yl)amide or N-(pyrimidin-4-yl)amide, as described herein, and a carrier, diluent, or excipient (e.g., a pharmaceutically acceptable carrier, diluent, or excipient; a physiologically acceptable carrier, diluent, or excipient; a cosmetic carrier, diluent, or excipient).

Another aspect of the present invention pertains to a method of preparing a composition (e.g., a pharmaceutical composition; a physiologically acceptable composition; a cosmetic composition) comprising mixing an N-(pyrid-4-yl)amide or N-(pyrimidin-4-yl)amide, as described herein, and a carrier, diluent, or excipient (e.g., a pharmaceutically acceptable carrier, diluent, or excipient; a physiologically acceptable carrier, diluent, or excipient; a cosmetic carrier, diluent, or excipient).

Uses

The N-(pyrid-4-yl)amides and N-(pyrimidin-4-yl)amides, as described herein, are useful, for example, in the treatment of disorders and diseases that are ameliorated by the inhibition of an androgen receptor, as described herein.

Use in Methods of Modulating (e.q., Inhibiting) an Androgen Receptor

Another aspect of the present invention pertains to a method of modulating (e.g., inhibiting) an androgen receptor, in vitro or in vivo, comprising contacting the androgen receptor with an effective amount of an N-(pyrid-4-yl)amide or N-(pyrimidin-4-yl)amide, as described herein.

Another aspect of the present invention pertains to a method of modulating (e.g., inhibiting) an androgen receptor in a cell, in vitro or in vivo, comprising contacting the cell with an effective amount of an N-(pyrid-4-yl)amide or N-(pyrimidin-4-yl)amide, as described herein.

Suitable assays for determining androgen receptor modulation (e.g., inhibition) are described herein and/or are known in the art.

In one embodiment, the method is performed in vitro.

In one embodiment, the method is performed in vivo.

In one embodiment, the N-(pyrid-4-yl)amide or N-(pyrimidin-4-yl)amide is provided in the form of a pharmaceutically acceptable composition.

Any type of cell may be treated, including but not limited to, skin, adipose, lung, gastrointestinal (including, e.g., bowel, colon), breast (mammary), ovarian, prostate, liver (hepatic), kidney (renal), bladder, pancreas, and brain.

One of ordinary skill in the art is readily able to determine whether or not a candidate compound modulates (e.g., inhibits) an androgen receptor. For example, suitable assays are described herein.

Use in Methods of Therapy

Another aspect of the present invention pertains to an N-(pyrid-4-yl)amide or N-(pyrimidin-4-yl)amide, as described herein, for use in a method of treatment of the human or animal body by therapy.

Use in the Manufacture of Medicaments

Another aspect of the present invention pertains to use of an N-(pyrid-4-yl)amide or N-(pyrimidin-4-yl)amide, as described herein, in the manufacture of a medicament for use in treatment.

In one embodiment, the medicament comprises the N-(pyrid-4-yl)amide or N-(pyrimidin-4-yl)amide.

Methods of Treatment

Another aspect of the present invention pertains to a method of treatment comprising administering to a patient in need of treatment a therapeutically effective amount of an N-(pyrid-4-yl)amide or N-(pyrimidin-4-yl)amide, as described herein, preferably in the form of a pharmaceutical composition.

Diseases and Disorders Ameliorated by the Modulation (e.g., Inhibition) of an Androgen Receptor Compounds that modulate (e.g., inhibit) an androgen receptor, for example, androgen receptor agonists and androgen receptor antagonists, are useful in the treatment of, for example, various hormone-dependent diseases and disorders (e.g., androgen-dependent diseases and disorders).

In one embodiment (e.g., of use in methods of therapy, of use in the manufacture of medicaments, of methods of treatment), the treatment is treatment of a disease or disorder that is ameliorated by the modulation (e.g., inhibition) of an androgen receptor.

In one embodiment, the treatment is treatment of an androgen-dependent disease or disorder.

Dermatological Diseases and Disorders

A number of dermatological diseases and disorders may be treated with compounds that modulate (e.g., inhibit) an androgen receptor.

In one embodiment, the treatment is treatment of a dermatological disease or disorder; a disease or disorder of the sebaceous gland(s); acne; hyperseborrhoea; oily skin; seborrhoeic dermatitis; hyperpilosity or hirsutism; atopic dermatitis; or androgenic alopecia.

In one embodiment, the treatment is treatment of a dermatological disease or disorder.

In one embodiment, the treatment is treatment of a disease or disorder of the sebaceous gland(s).

In one embodiment, the treatment is treatment of acne.

In one embodiment, the treatment is treatment of hyperseborrhoea.

In one embodiment, the treatment is treatment of oily skin.

In one embodiment, the treatment is treatment of seborrhoeic dermatitis.

In one embodiment, the treatment is treatment of hyperpilosity or hirsutism.

In one embodiment, the treatment is treatment of atopic dermatitis.

In one embodiment, the treatment is treatment of androgenic alopecia.

Additional Hormone-Dependent Diseases and Disorders

In one embodiment, the treatment is treatment of a hormone-dependent cancer, such as prostate or breast cancer.

In one embodiment, the treatment is treatment of a benign hyperplasia of the prostate gland, premature puberty, virilisation, polycystic ovary syndrome, Stein-Lelventhal syndrome, loss of libido, or endometriosis.

In one embodiment, the treatment is treatment of loss of muscular mass (sarcopaenia), muscular atrophy, impotence, masculine sterility, abnormal masculine differentiation (hermaphrodism), hypogonadism, or osteoporosis.

Treatment

The term "treatment," as used herein in the context of treating a disorder, pertains generally to treatment and therapy, whether of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of acne, reducing the incidence of acne, alleviating the symptoms of acne, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

For example, the N-(pyrid-4-yl)amides and N-(pyrimidin-4-yl)amides described herein may be used alone or in combination, for example, one or more of:
an antibiotic product, such as erythromycin or fusidic acid;
azelaic acid or a derivative thereof;
a retinoid or retinoid derivative for the treatment of acne, such as tretinoin, adapalene, or tazarolene;
an inhibitor of 5α-reductase, such as (5α, 17β)-N-1,1-dimethylethyl-3-oxo-4-aza-androst-1-ene-17-carboxamide (also known as finasteride, Proscar, and Propecia);
an androgen receptor blocking agent for the treatment of acne, alopecia or hirsutism;
a product stimulating the growth of hair or for the treatment of alopecia, such as 6-piperidin-1-ylpyrimidine-2,4-diamine 3-oxide (also known as minoxidil).

Non-Therapeutic and Cosmetic Uses

The N-(pyrid-4-yl)amides and N-(pyrimidin-4-yl)amides, as described herein, are also useful in the field of cosmetics, especially in body care and hair care, and more especially for the treatment of skin with an acneic tendency.

Another aspect of the present invention pertains to a physiologically acceptable composition (e.g., a cosmetic composition) comprising an N-(pyrid-4-yl)amide or N-(pyrimidin-4-yl)amide, as described herein, and a physiologically acceptable carrier, diluent, or excipient (e.g., a cosmetic carrier, diluent, or excipient).

The terms "physiologically acceptable" and "cosmetic," as used herein, pertains to compounds, ingredients, materials, compositions, dosage forms, etc., which are, within the scope of sound medical judgment, suitable for cosmetic use in contact with the tissues (e.g., skin, hair, nails, mucosa, etc.) of the subject in question (e.g., human) without excessive toxicity, irritation, allergic response, or other problem or complication, commensurate with a reasonable benefit/risk ratio. Each physiologically acceptable (e.g., cosmetic) carrier, diluent, excipient, etc. must also be "acceptable" in the sense that it is compatible with the other ingredients of the formulation.

The physiologically acceptable composition (e.g., cosmetic composition) is a composition compatible with the skin and, as necessary, with its appendages (lashes, nails, hair) and/or mucous membranes.

The physiologically acceptable composition (e.g., cosmetic composition) may be in the form of, for example, an ointment, a cream, a milk, a pomade, a gel, a suspension (e.g., a microsphere or nanosphere suspension), lipidic or polymeric blisters or polymeric or gelled patches allowing controlled release, a powder, a lipidic or polymeric blister, an alcohol swab, a syndet, a solution, a spray, a mousse, a stick, a soap, a cleansing base, or a shampoo.

The concentration of the N-(pyrid-4-yl)amide or N-(pyrimidin-4-yl)amide in the physiologically acceptable composition (e.g., cosmetic composition) is preferably between 0.001% and 3% by weight relative to the total weight of the composition.

Another aspect of the present invention pertains to a non-therapeutic method (e.g., a cosmetic method) of body care and/or hair care comprising applying to a subject's body and/or hair an effective amount of an N-(pyrid-4-yl)amide or N-(pyrimidin-4-yl)amide, as described herein, preferably in the form of a physiologically acceptable composition (e.g., a cosmetic composition).

Another aspect of the present invention pertains to use of an N-(pyrid-4-yl)amide or N-(pyrimidin-4-yl)amide, as described herein, in a non-therapeutic method (e.g., a cosmetic method) of body care and/or hair care.

Another aspect of the present invention pertains to an N-(pyrid-4-yl)amide or N-(pyrimidin-4-yl)amide, as described herein, for use in a non-therapeutic method (e.g., a cosmetic method) of body care and/or hair care.

Another aspect of the present invention pertains to use of an N-(pyrid-4-yl)amide or N-(pyrimidin-4-yl)amide, as described herein, in the manufacture of physiologically acceptable composition (e.g., a cosmetic composition) for use in a non-therapeutic method of body care and/or hair care.

Another aspect of the present invention pertains to a non-therapeutic method (e.g., a cosmetic method) of body care and/or hair care, comprising applying to the body and/or hair of a subject an effective amount of a physiologically acceptable composition (e.g., a cosmetic composition) comprising an N-(pyrid-4-yl)amide or N-(pyrimidin-4-yl)amide, as described herein.

Another aspect of the present invention pertains to use of a physiologically acceptable composition (e.g., a cosmetic composition) comprising an N-(pyrid-4-yl)amide or N-(pyrimidin-4-yl)amide, as described herein in a non-therapeutic method (e.g., a cosmetic method) of body care and/or hair care.

Another aspect of the present invention pertains to a physiologically acceptable composition (e.g., a cosmetic composition) comprising an N-(pyrid-4-yl)amide or N-(pyrimidin-4-yl)amide, as described herein, for use in a non-therapeutic method (e.g., a cosmetic method) of body care and/or hair care.

Other Uses

The N-(pyrid-4-yl)amides and N-(pyrimidin-4-yl)amides described herein may also be used as cell culture additives to modulate (e.g., inhibit) an androgen receptor, etc.

The N-(pyrid-4-yl)amides and N-(pyrimidin-4-yl)amides described herein may also be used as part of an in vitro assay, for example, in order to determine whether a candidate host is likely to benefit from treatment with the compound in question.

The N-(pyrid-4-yl)amides and N-(pyrimidin-4-yl)amides described herein may also be used as a standard, for example, in an assay, in order to identify other active compounds, other modulators (e.g., inhibitors) of an androgen receptor, etc.

Kits

Another aspect of the invention pertains to a kit comprising (a) an N-(pyrid-4-yl)amide or N-(pyrimidin-4-yl)amide as described herein, or a composition (e.g., a pharmaceutical composition; a physiologically acceptable composition; a cosmetic composition) comprising an N-(pyrid-4-yl)amide or N-(pyrimidin-4-yl)amide as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The N-(pyrid-4-yl)amide or N-(pyrimidin-4-yl)amide or pharmaceutical composition comprising the N-(pyrid-4-yl)amide or N-(pyrimidin-4-yl)amide may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In some preferred embodiments, the compound or composition is administered transdermally and/or transmucosally, e.g., to skin and/or mucous membrane of the subject/patient.

For such embodiments, the compound or composition may suitable be applied in the form of an ointment, a cream, a milk, a pomade, a gel, a suspension (e.g., a microsphere or nanosphere suspension), lipidic or polymeric blisters or polymeric or gelled patches allowing controlled release, a powder, a lipidic or polymeric blister, an alcohol swab, a syndet, a solution, a spray, a mousse, a stick, a soap, a cleansing base, or a shampoo.

For such embodiments, the compound is present in the composition at a concentration generally ranging from 0.001% to 30% by weight, and preferably from 0.01% to 10% by weight, relative to the total weight of the composition.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

In one preferred embodiment, the subject/patient is a human.

Formulations

While it is possible for the compound to be administered alone, it is preferable to present it as a pharmaceutical formulation (e.g., composition, preparation, medicament) comprising at least one N-(pyrid-4-yl)amide or N-(pyrimidin-4-yl)amide, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one N-(pyrid-4-yl)amide or N-(pyrimidin-4-yl)amide, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous) (including, e.g., microsphere and nanosphere suspensions), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the N-(pyrid-4-yl)amide or N-(pyrimidin-4-yl)amide, and compositions comprising the N-(pyrid-4-yl)amide or N-(pyrimidin-4-yl)amide, can vary from patient to patient. Determining the optimal dosage will generally involve the balancing of the level of therapeutic benefit against any risk or deleterious side effects. The selected dosage level will depend on a variety of factors including, but not limited to, the activity of the particular N-(pyrid-4-yl)amide or N-(pyrimidin-4-yl)amide, the route of administration, the time of administration, the rate of excretion of the N-(pyrid-4-yl)amide or N-(pyrimidin-4-yl)amide, the duration of the treatment, other drugs, compounds, and/or materials used in combination, the severity of the disorder, and the species, sex, age, weight, condition, general health, and prior medical history of the patient. The amount of -(pyrid-4-yl)amide or N-(pyrimidin-4-yl)amide and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the N-(pyrid-4-yl)amide or N-(pyrimidin-4-yl)amide is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Synthesis 1

2-Hydroxy-2-methyl-pentanoic acid (2-bromo-pyridin-4-yl)-amide (Compound 1)

Preparation According to Scheme 1, Method 1a.
Step 1.1
N-(2-bromo-pyridin-4-yl)-2-oxo-propionamide 2.8 g (32.2 mmol, 2 eq) of pyruvic acid (initial product 1) were poured into a 50 mL single collar flask, 20 mL of thionyl was added to this and it was heated at reflux for 2 hours. After 2 hours, the reaction mixture was dry concentrated by azeotroping several times with dry toluene. 2.8 g (16.1 mmol, 1 eq) of 2-bromo-pyridin-4-ylamine (initial product 2), diluted in 5 mL of pyridine, was then added, drop-by-drop at 0° C., and the mixture agitated at ambient temperature for 16 hours. The reaction mixture was diluted with 50 mL of ethyl acetate, washed with 50 mL of an aqueous solution of saturated sodium bicarbonate, followed by 3×50 mL of water. The organic phase was dry concentrated. The residue was chromatographed on silica with a heptanes/ethyl acetate mixture (2/1 v/v) as eluent. N-(2-bromo-pyridin-4-yl)-2-oxo-propionamide was obtained in the form of a white solid.

Step 1.2

2-Hydroxy-2-methyl-pentanoic acid (2-bromo-pyridin-4-yl)-amide 170 mg (0.70 mmol, 1 eq) of N-(2-bromo-pyridin-4-yl)-2-oxo-propionamide was poured into a three-collar flask and 5 mL of tetrahydrofuran added and the mixture cooled to 0° C. 1.1 mL (2.0 mmol, 3 eq) of a solution of magnesium bromide magnesium (initial product 3) (2 M) was added to the tetrahydrofuran drop-by-drop and agitated for 1 hour and 30 minutes at ambient temperature. The reaction mixture was cooled to 0° C. and 25 mL of an aqueous solution of hydrochloric acid (1 M) was added. The organic phases were extracted with 2×50 mL of ethyl acetate, washed with 2×50 mL of water, dried over magnesium sulphate, and dry concentrated. A yellow oil was obtained which was chromatographed on silica with a heptanes/ethyl acetate mixture (1/1 v/v) as eluent. 2-hydroxy-2-methyl-pentanoic acid (2-bromo-pyridin-4-yl)-amide was obtained in the form of a white solid.

Melting point=102° C. NMR ($^1$H, DMSO): 0.82-0.86 (t; 3H; J=8 Hz); 1.14-1.17 (m; 1H); 1.41 (s; 3H)1.41-1.44 (m; 1H); 1.49-156 (m; 1H); 1.67-1.70 (m; 1H) 5.74 (s; 1H); 7.81-7.83 (d; 1H; J=8 HZ); 8.13 (s; 1H); 8.21-8.23 (d; 1H; J=8 Hz); 10.15 (s; 1H).

Syntheses 2 to 51

Syntheses 2 to 51 are described in Table 1 below. The compounds were synthesised according to the above procedure by replacing the initial products 1, 2 and 3 referred to in Synthesis 1 by the initial products mentioned in Table 1. In the context of the $^1$H NMR data shown in Table 1, s=singlet, d=doublet, t=triplet, m=multiplet, q=quartet, J=coupling constant in hertz (Hz).

TABLE 1

| Cmpd. No. | Chemical Name | Initial Product 1 | Initial Product 2 | Initial Product 3 | Melting point (° C.) | $^1$H NMR 400 Mhz |
|---|---|---|---|---|---|---|
| 2 | 2-Ethyl-2-hydroxy-5-methyl-hexanoic acid (2-bromo-pyridin-4-yl)-amide | Keto butyric acid | 2-Bromo-pyridin-4-ylamine | Magnesium isopentyl bromide | Oil | (DMSO) 0.84-0.78 (m, 9H); 0.9-1.0 (m, 1H); 1.3-1.5 (m, 2H); 1.5-1.6 (m, 2H); 1.7 1.8 (m, 2H); 5.5 (s, 1H); 7.8 (dd, 1H, J = 1.8 Hz); 8.1 (d, 1H, J = 1.7 Hz); 8.2 (d, 1H, J = 5.6 Hz); 10.1 (s, 1H) |
| 3 | N-(2-Bromo-pyridin-4-yl)-2-hydroxy-2-(4-methoxy-phenyl)-propionamide | Pyruvic acid | 2-Bromo-pyridin-4-ylamine | 4-methoxy-phenyl magnesium bromide | 66 | (DMSO) 1.68 (s, 3H); 3.72 (s, 3H); 6.55 (s, 1H); 6.9 (m, 2H); 7.49 (m, 2H); 7.79 (dd, 1H, J = 1.8 Hz); 8.09 (d, 1H, J = 1.7 Hz); 8.19 (d, 1H, J = 5.6 Hz); 10.3 (s, 1H) |
| 4 | 2-Hydroxy-2,4-dimethyl-pentanoic acid (2-bromo-pyridin-4-yl)-amide | Pyruvic acid | 2-Bromo-pyridin-4-ylamine | Magnesium isobutyl chloride | oil | (DMSO) 0.78 (m, 3H); 0.90 (m, 3H); 1.33 (s, 3H); 1.45-1.55 (m, 1H); 1.7-1.8 (m, 2H); 5.7 (s, 1H); 7.82 (dd, 1H, J = 1.8 Hz); 8.13 (d, 1H, J = 1.7 Hz); 8.22 (d, 1H, J = 5.6 Hz); 10.2 (s, 1H) |
| 5 | 2-Ethyl-2-hydroxy-hexanoic acid (2-bromo-6-methoxy-pyridin-4-yl)-amide | Keto butyric acid | 2-Bromo-6-methoxy-pyridin-4-ylamine | Magnesium n-butyl bromide | 101 | (DMSO) 0.77-0.85 (m, 6 H), 1.0-1.1 (m, 1 H), 1.20-1.25 (m, 2 H), 1.32-1.57 (m, 3 H), 1.68-1.77 (m, 2 H), 3.80 (s, 3 H), 5.46 (s, 1 H), 7.33 (d, 1 H, J = 1.5 Hz), 7.74 (d, 1 H, J = 1.5 Hz), 10.01 (1 H, s) |

TABLE 1-continued

| Cmpd. No. | Chemical Name | Initial Product 1 | Initial Product 2 | Initial Product 3 | Melting point (° C.) | $^1$H NMR 400 Mhz |
|---|---|---|---|---|---|---|
| 6 | 2-Hydroxy-2-propyl-pentanoic acid (2-bromo-pyridin-4-yl)-amide | 2-Oxo pentanoic acid | 2-Bromo-pyridin-4-ylamine | Magnesium propyl bromide | oil | (DMSO) 0.83 (t, 6H, J = 7.2 Hz); 1.07-1.11 (m, 2H); 1.43-1.54 (m, 4H); 1.67-1.71 (m, 2H); 5.5 (s, 1H); 7.82 (dd, 1H, J = 1.8 Hz), 8.13 (d, 1H, J = 1.7 Hz); 8.21 (d, 1H, J = 5.6 Hz); 10.1 (s, 1H) |
| 7 | N-(2-Bromo-pyridin-4-yl)-2-cyclohexyl-2-hydroxy-butyramide | Keto butyric acid | 2-Bromo-pyridin-4-ylamine | Magnesium cyclohexyl bromide | oil | (DMSO) 0.78 (t, 3H, J = 7.3 Hz); 1.0-1.25 (m, 5H); 1.35-1.45 (m, 1H); 1.55-1.85 (m, 7H); 5.3 (s, 1H); 7.8 (d, 1H, J = 1.7 Hz); 8.14 (d, 1H, J = 1.7 Hz); 8.21 (d, 1H, J = 5.6 Hz); 10 (s, 1H) |
| 8 | 2-Hydroxy-2-methyl-hexanoic acid (2-bromo-6-methoxy-pyridin-4-yl)-amide | Pyruvic acid | 2-Bromo-6-methoxy-pyridin-4-ylamine | Magnesium n-butyl chloride | 98 | (CHCl$_3$) 0.89-092 (t, 3H, J = 7.1 Hz), 1.19-1.45 (m, 4H), 1.51 (s, 3H), 1.60-1.68 (m, 1H), 1.93-2.0 (m, 1H), 3.93 (s, 3H), 7.03 (d, 1H), 7.36 (d, 1H), 8.82 (s, 1H) |
| 9 | N-(2-Bromo-6-methoxy-pyridin-4-yl)-2-cyclopentyl-2-hydroxy-butyramide | Keto butyric acid | 2-Bromo-6-methoxy-pyridin-4-ylamine | Magnesium cyclopentyl bromide | Not determined | (DMSO) 0.8 (t; 3H; J = 8 Hz); 1.4-1.6 (m; 9H); 1.8 (m; 1H); 2.2 (m; 1H); 3.8 (s; 3H); 5.3 (s; 1H); 7.3 (d; 1H; J = 1.4 Hz); 7.7 (d; 1H; J = 1.4 Hz); 10.0 (s; 1H) |
| 10 | N-(2-Bromo-pyridin-4-yl)-2-hydroxy-2-(2-methoxy-phenyl)-propionamide | Pyruvic acid | 2-Bromo-pyridin-4-ylamine | Magnesium 2-methoxy-phenyl bromide | 63 | (DMSO) 1.66 (s, 3H); 3.61 (s, 3H); 6.05 (s, 1H); 6.96-6.99 (m, 2H); 7.28-7.32 (m, 1H); 7.51 (m, 1H); 7.79 (dd, 1H, J = 1.8 Hz); 8.08 (d, 1H, J = 1.7 Hz); 8.20 (d, 1H, J = 5.6 Hz); 10.1 (s, 1H) |
| 11 | 2-Hydroxy-2-methyl-pentanoic acid (2,6-dimethoxy-pyrimidin-4-yl)-amide | Pyruvic acid | 2,6-Dimethoxy-pyrimidin-4-ylamine | Magnesium propyl bromide | 147 | (DMSO) 0.9 (t; 3H; J = 8 Hz); 1.0-1.2 (m; 1H); 1.3 (s; 3H); 1.4-1.5 (m; 1H); 1.5-1.6 (m; 1H); 1.7 (m; 1H); 3.86 (s; 3H); 3.88 (s; 3H); 6.0 (s; 1H) 7.1 (s; 1H); 9.4 (s; 1H) |
| 12 | 2-Hydroxy-2-methyl-octanoic acid (2-bromo-6-methoxy-pyridin-4-yl)-amide | Pyruvic acid | 2-Bromo-6-methoxy-pyridin-4-ylamine | Magnesium n-hexyl bromide | oil | (DMSO) 0.83 (t, 3H, J = 7.0 Hz); 1.05-1.15 (m, 1H); 1.2-1.3 (m, 6H); 1.3 (s, 3H); 1.35-1.45 (m, 1H); 1.5-1.6 (m, 1H); 1.65-1.75 (m, 1H); 3.8 (s, 3H); 5.7 (s, 1H); 7.32 (d, 1H, J = 1.4 Hz); 7.73 (d, 1H, J = 1.4 Hz); 10.1 (s, 1H) |

TABLE 1-continued

| Cmpd. No. | Chemical Name | Initial Product 1 | Initial Product 2 | Initial Product 3 | Melting point (° C.) | $^1$H NMR 400 Mhz |
|---|---|---|---|---|---|---|
| 13 | N-(2-Bromo-6-methoxy-pyridin-4-yl)-2-ethyl-2-hydroxy-3-methyl-butyramide | Keto butyric acid | 2-Bromo-6-methoxy-pyridin-4-ylamine | Magnesium isopropyl bromide | 114 | (DMSO) 0.76-0.80 (m, 6H), 0.87-0.88 (d, 3H, J = 6.8 Hz), 1.58-1.78 (m, 2H), 1.9-2.0 (m, 1H), 3.80 (s, 3H), 5.30 (s, 1H), 7.33 (d, 1H, J = 1.5 Hz), 7.74 (d, 1H, J = 1.5 Hz), 9.98 (1 H, s) |
| 14 | N-(2-Bromo-pyridin-4-yl)-2-hydroxy-2-methyl-propionamide | Pyruvic acid | 2-Bromo-pyridin-4-ylamine | Magnesium methyl iodide | 150 | (CDCl$_3$) 1.5 (s; 6H); 2.6 (s; 1H); 7.4 (dd; 1H; J = 5.6, 1.8 Hz); 7.85 (s; 1H); 8.2 (d; 1H; J = 5.6 Hz) |
| 15 | N-(2-Bromo-pyridin-4-yl)-2-hydroxy-2-methyl-butyramide | Pyruvic acid | 2-Bromo-pyridin-4-ylamine | Magnesium ethyl bromide | 108 | (CDCl$_3$) 0.9 (t; 3H; J = 8 Hz); 1.5 (s; 3H); 1.6-1.7 (m; 1H); 1.9-2.0 (m; 1H); 7.4 (d; 1H; J = 4 Hz); 7.8 (s; 1H); 8.2 (d; 1H; J = 4 Hz); 8.8 (s; 1H) |
| 16 | 2-Ethyl-2-hydroxy-4-methyl-pentanoic acid (2-bromo-6-methoxy-pyridin-4-yl)-amide | Keto butyric acid | 2-Bromo-6-methoxy-pyridin-4-ylamine | Magnesium isobutyl bromide | 114 | (DMSO) 0.73-0.79 (m, 6H), 0.89-0.91 (d, 3H, J = 6.4 Hz), 1.43-1.53 (m, 2H), 1.68-1.77 (m, 3H), 3.80 (s, 3 H), 5.46 (s, 1 H), 7.34 (d, 1 H, J = 1.5 Hz), 7.74 (d, 1 H, J = 1.5 Hz), 10.08 (1 H, s). |
| 17 | N-(2-Bromo-pyridin-4-yl)-2-cyclopentyl-2-hydroxy-propionamide | Pyruvic acid | 2-Bromo-pyridin-4-ylamine | Magnesium cyclopentyl bromide | oil | (DMSO) 1.32 (s, 3H); 1.39-1.53 (m, 8H); 2.2 (m, 1H); 5.76 (s, 1H); 7.82 (q, 1H, J = 1.8 Hz); 8.13 (d, 1H, J = 1.7 Hz); 8.22 (d, 1H, J = 5.6 Hz); 10.2 (s, 1H) |
| 18 | 2-Hydroxy-2-methyl-heptanoic acid (2-bromo-6-methoxy-pyridin-4-yl)-amide | Pyruvic acid | 2-Bromo-6-methoxy-pyridin-4-ylamine | Magnesium n-pentyl bromide | 81 | (DMSO) 0.83 (t, 3H, J = 7.1 Hz); 1.17-125 (m, 5H); 1.31 (s, 3H); 1.35-1.45 (m, 1H); 1.50-1.55 (m, 1H); 1.65-1.75 (m, 1H); 3.8 (s, 3H); 5.71 (s, 1H); 7.32 (d, 1H, J = 1.4 Hz); 7.73 (d, 1H, J = 1.4 Hz); 10.1 (s, 1H) |
| 19 | 2-Ethyl-2-hydroxy-pentanoic acid (2-bromo-6-methoxy-pyridin-4-yl)-amide | Keto butyric acid | 2-Bromo-6-methoxy-pyridin-4-ylamine | Magnesium propyl bromide | 79 | (DMSO) 0.62-0.70 (6 H, m), 0.85-1.0 (1 H, m), 1.31-1.41 (3 H, m), 1.52-1.60 (2H, m), 3.65 (3 H, s), 5.35 (1 H, s), 7.18 (1 H, d, J = 1.5 Hz), 7.59 (1 H, d, J = 1.5 Hz), 9.90 (1H, S). |
| 20 | 2-Hydroxy-2,4-dimethyl-pentanoic acid (2-methoxy-pyridin-4-yl)-amide | Pyruvic acid | 2-Methoxy-pyridin-4-ylamine | Magnesium isobutyl bromide | 135 | (DMSO) 0.8 (d; 3H; J = 8 Hz); 0.9 (d; 3H; J = 8 Hz); 1.3 (s; 3H); 1.5 (m; 1H); 1.7-1.8 (m; 2H); 3.8 (s; 3H); 5.7 (s; 1H); 7.3 (s; 1H); 7.4 (d; |

TABLE 1-continued

| Cmpd. No. | Chemical Name | Initial Product 1 | Initial Product 2 | Initial Product 3 | Melting point (° C.) | ¹H NMR 400 Mhz |
|---|---|---|---|---|---|---|
| | | | | | | 1H; J = 6 Hz); 8.0 (d; 1H; J = 6 Hz); 9.9 (s; 1H) |
| 21 | N-(2-Bromo-6-methoxy-pyridin-4-yl)-2-cyclopentyl-2-hydroxy-propionamide | Pyruvic acid | 2-Bromo-6-methoxy-pyridin-4-ylamine | Magnesium cyclopentyl bromide | n/d | (DMSO) 1.3 (s; 3H); 1.4-1.6 (m; 3H); 2.2 (m; 1H); 3.8 (s; 3H); 5.7 (s; 1H); 7.3 (d; 1H; J = 1.4 Hz); 7.7 (d; 1H; J = 1.4 Hz); 10.1 (s; 1H) |
| 22 | N-(2-Bromo-6-methoxy-pyridin-4-yl)-2-ethyl-2-hydroxy-butyramide | Keto butyric acid | 2-Bromo-6-methoxy-pyridin-4-ylamine | Magnesium ethyl bromide | 123 | (DMSO) 0.78-0.81 (t, 6 H, J = 7.4 Hz), 1.52-1.57 (m, 2 H), 1.71-1.76 (m, 2 H), 3.80 (s, 3 H), 5.44 (s, 1 H), 7.33 (d, 1 H, J = 1.5 Hz), 7.74 (d, 1 H, J = 1.5 Hz), 10.02 (1 H, s). |
| 23 | 2-Butyl-2-hydroxy-hexanoic acid (2-bromo-pyridin-4-yl)-amide | 2-aceto hexanoic acid | 2-Bromo-pyridin-4-ylamine | Magnesium n-butyl bromide | oil | (DMSO) 0.82 (t, 6H, J = 7.4 Hz); 1.0-1.1 (m, 2H); 1.22 (m, 4H); 1.35-1.4 (m, 2H); 1.5-1.55 (m, 2H); 1.7-1.8 (m, 2H); 5.49 (s, 1H); 7.8 (s, 1H); 8.13 (d, 1H, J = 1.6 Hz); 8.21 (d, 1H, J = 5.6 Hz); 10.1 (s, 1H) |
| 24 | N-(2-Bromo-pyridin-4-yl)-2-hydroxy-4-(4-methoxy-phenyl)-2-methyl-butyramide | Pyruvic acid | 2-Bromo-pyridin-4-ylamine | Magnesium 4-methoxy-phenyl methyl | oil | (DMSO) 1.37 (s, 3H); 1.75-1.85 (m, 1H); 1.95-2.05 (m, 1H); 2.35-2.45 (m, 1H); 2.6 2.7 (m, 1H); 3.68 (s, 3H); 6.0 (m, 1H); 6.79 (m, 2H); 7.07 (m, 2H); 7.81 (dd, 1H, J = 1.8 Hz); 8.12 (d, 1H, J = 1.7 Hz); 8.22 (d, 1H, J = 5.6 Hz); 10.2 (s, 1H) |
| 25 | N-(2-Bromo-6-methoxy-pyridin-4-yl)-2-hydroxy-2,3-dimethyl-butyramide | Pyruvic acid | 2-Bromo-6-methoxy-pyridin-4-ylamine | Magnesium isopropyl bromide | 152 | (CDCl₃) 0.92-0.93 (d, 3 H, J = 6.9 Hz), 0.99-1.00 (d, 3 H, J = 6.9 Hz), 1.48 (s, 3 H), 1.93 (s, 1 H), 2.15-2.18 (m, 1 H), 3.93 (s, 3 H), 7.02 (d, 1 H, J = 1.5 Hz), 7.36 (d, 1 H, J = 1.5 Hz), 8.78 (s, 1 H) |
| 26 | N-(2-Bromo-6-methoxy-pyridin-4-yl)-2-hydroxy-2-methyl-4-phenyl-butyramide | Pyruvic acid | 2-Bromo-6-methoxy-pyridin-4-ylamine | Magnesium phenethyl chloride | oil | (CDCl₃) 1.56 (s, 3H), 1.94, 2.0 (m, 1 H), 2.31-2.39 (m, 1 H), 2.62-2.65 (m, 1 H), 2.75-2.79 (m, 1 H), 3.94 (s, 3 H), 7.02 (d, 1 H, J = 1.5 Hz), 7.18-7.35 (m, 5 H), 7.36 (d, 1 H, J = 1.5 Hz), 8.80 (1 H, s) |

TABLE 1-continued

| Cmpd. No. | Chemical Name | Initial Product 1 | Initial Product 2 | Initial Product 3 | Melting point (° C.) | ¹H NMR 400 Mhz |
|---|---|---|---|---|---|---|
| 27 | 2-(4-Fluoro-phenyl)-2-hydroxy-N-(2-methoxy-pyridin-4-yl)-propionamide | Pyruvic acid | 2-Methoxy-pyridin-4-ylamine | Magnesium 4-fluorophenyl bromide | 175 | (DMSO) 1.7 (s; 3H); 3.8 (s; 3H); 6.7 (s; 1H); 7.2 (Tr; 2H; J = 8 Hz); 7.3 (s; 1H); 7.4 (d; 1H; J = 8 Hz); 7.6 (m; 2H); 8.0 (d; 1H; J = 8 Hz); 10.1 (s; 1H) |
| 28 | N-(2-Bromo-pyridin-4-yl)-2-hydroxy-4-(2-methoxy-phenyl)-2-methyl-butyramide | Pyruvic acid | 2-Bromo-pyridin-4-ylamine | Magnesium 2-methoxy-phenyl ethyl bromide | oil | (DMSO) 1.38 (s, 3H); 1.77-1.78 (m, 1H); 1.96-1.97 (m, 1H); 2.41-2.42 (m, 1H); 2.71-2.72 (m, 1H); 3.73 (s, 3H); 5.88 (s, 1H); 6.8-6.84 (m, 1H); 6.89-6.91 (d, 1H, J = 8.1 Hz); 7.08 (dd, 1H, J = 1.5 Hz); 7.12-7.16 (m, 1H); 7.82 (dd, 1H, J = 1.8 Hz); |
| 29 | 2-Hydroxy-2-propyl-pentanoic acid (2-bromo-6-methoxy-pyridin-4-yl)-amide | 2-Oxo pentanoic acid | 2-Bromo-6-methyl-pyridin-4-ylamine | Magnesium propyl chloride | oil | (DMSO) 0.8 (t; 6H; J = 8 Hz); 1.1 (m; 2H); 1.4-1.5 (m; 2H); 1.7 (m; 2H); 3.8 (s; 3H); 5.5 (s; 1H); 7.3 (d; 1H; J = 1.4 Hz); 7.7 (d; 1H; J = 1.4 Hz); 10 (s; 1H) |
| 30 | 3-(4-Fluoro-phenyl)-2-hydroxy-N-(2-methoxy-pyridin-4-yl)-2-methyl-propionamide | Pyruvic acid | 2-Methoxy-pyridin-4-ylamine | Magnesium 4-fluorophenyl bromide | 175 | (DMSO) 1.3 (s; 3H); 2.8 (d; 1H; J = 13.4); 3.0 (d; 1H; J = 13.4 Hz); 3.8 (s; 3H); 5.9 (s; 1H); 7.1 (t; 2H; J = 9 Hz); 7.2 (m; 3H); 7.3 (m; 1H); 8.0 (d; 1H; J = 6 Hz) 9.7 (s; 1H) |
| 31 | N-(2-Bromo-pyridin-4-yl)-2-ethyl-2-hydroxy-butyramide | Keto butyric acid | 2-Bromo-pyridin-4-ylamine | Magnesium ethyl bromide | oil | (CDCl₃) 1.0 (t; 6H; J = 4 Hz); 1.6-1.7 (m; 2H); 2.0-2.1 (m; 2H); 7.5 (d; 1H; J = 6 Hz); 7.9 (s; 1H); 8.3 (d; 1H; J = 6 Hz); 8.9 (s; 1H) |
| 32 | N-(2-Bromo-pyridin-4-yl)-2-hydroxy-2-phenyl-propionamide | Pyruvic acid | 2-Bromo-pyridin-4-ylamine | Magnesium phenyl bromide | n/d | (CDCl₃) 1.9 (s; 3H); 3.0 (s; 1H); 7.3-7.4 (m; 4H); 7.5 (m; 2H) 7.8 (s; 1H); 8.1 (d; 1H; J = 4 Hz); 8.8 (s; 1H) |
| 33 | N-(2-Bromo-pyridin-4-yl)-2-hydroxy-2-methyl-3-phenyl-propionamide | Pyruvic acid | 2-Bromo-pyridin-4-ylamine | Magnesium benzyl bromide | oil | (DMSO) 1.34 (s, 3H); 2.85 (d, 1H, J = 13.3 Hz); 3.03 (d, 1H, J = 13.3 hz); 6.0 (m, 1H); 7.16-7.24 (m, 5H); 7.75 (dd, 1H, J = 1.8 Hz); 8.05 (d, 1H, J = 1.8 Hz); 8.19 (d, 1H, J = 5.6 Hz); 10.1 (s, 1H) |
| 34 | 2-Hydroxy-2-methyl-heptanoic acid (2-bromo-pyridin-4-yl)-amide | Pyruvic acid | 2-Bromo-pyridin-4-ylamine | Magnesium n-pentyl bromide | oil | (DMSO) 0.83 (t, 3H, J = 7 Hz); 1.10-1.27 (m, 5H); 1.32 (s, 3H); 1.37-1.43 (m, 1H); 1.49-1.56 (m, 1H); 1.67-1.73 (m, 1H); 5.7 (s, 1H); 7.82 (dd, 1H, |

TABLE 1-continued

| Cmpd. No. | Chemical Name | Initial Product 1 | Initial Product 2 | Initial Product 3 | Melting point (° C.) | $^1$H NMR 400 Mhz |
|---|---|---|---|---|---|---|
| | | | | | | J = 1.6 Hz); 8.12 (d, 1H, J = 1.4 Hz); 8.22 (d, 1H, J = 5.6 Hz); 10.2 (s, 1H) |
| 35 | N-(2-Bromo-pyridin-4-yl)-2-hydroxy-2-(3-methoxy-phenyl)-propionamide | Pyruvic acid | 2-Bromo-pyridin-4-ylamine | Magnesium 3-methoxy-pentyl bromide | oil | (DMSO) 1.69 (s, 3H); 3.75 (s, 3H); 6.63 (s, 1H); 6.83-6.86 (m, 1H); 7.1-7.2 (m, 2H); 7.26 (m, 1H); 7.8 (dd, 1H, J = 1.8 Hz); 8.09 (d, 1H, J = 1.7 Hz); 8.19 (d, 1H, J = 5.6 Hz); 10.4 (s, 1H) |
| 36 | 2-Ethyl-2-hydroxy-pentanoic acid (2-methoxy-pyridin-4-yl)-amide | Keto butyric acid | 2-Methoxy-pyridin-4-ylamine | Magnesium propyl bromide | n/d | (DMSO) 0.8-0.9 (m; 6H); 1.0-1.2 (m; 1H); 1.5-1.6 (m; 3H); 1.7-1.8 (m; 2H); 5.4 (s; 1H); 7.3; (s; 1H); 7.4 (d; 1H; J = 6 HZ); 8.0 (d; 1H; J = 6 Hz); 9.8 (s; 1H) |
| 37 | N-(2-Bromo-pyridin-4-yl)-2-hydroxy-4-(3-methoxy-phenyl)-2-methyl-butyramide | Pyruvic acid | 2-Bromo-pyridin-4-ylamine | Magnesium 3-methoxy-phenethyl bromide | oil | (DMSO) 1.38 (s, 3H); 1.8-1.9 (m, 1H); 2.0 (m, 1H); 2.7 (m, 1H); 3.7 (s, 3H); 6.0 (s, 1H); 6.72 (t, 3H, J = 1.1 Hz); 7.15 (m, 1H); 7.82 (dd, 1H, J = 1.8 Hz); 8.12 (d, 1H, J = 1.7 Hz); 8.22 (d, 1H, J = 5.6 Hz); 10.2 (s, 1H) |
| 38 | N-(2-Bromo-6-methoxy-pyridin-4-yl)-2-hydroxy-2-methyl-propionamide | Pyruvic acid | 2-Bromo-6-methoxy-pyridin-4-ylamine | Magnesium methyl bromide | 104 | (DMSO) 1.33 (s, 6 H), 3.80 (s, 3 H), 5.86 (s, 1 H), 7.32 (d, 1 H, J = 1.5 Hz), 7.72 (d, 1 H, J = 1. Hz), 10.1 (1 H, s) |
| 39 | 2-Hydroxy-2-methyl-pentanoic acid (2-methoxy-pyridin-4-yl)-amide | Pyruvic acid | 2-Methoxy-pyridin-4-ylamine | Magnesium propyl bromide | 101 | (DMSO) 0.9 (t; 3H; J = 8 Hz); 1.1-1.2 (m; 1H); 1.3 (s; 1H); 1.4-1.5 (m; 1H); 1.5-1.6 (m; 1H); 1.7 (m; 1H); 3.8 (s; 3H); 5.7 (s; 1H) 7.3 (s; 1H); 7.4 (d; 1H; J = 6 Hz); 8.0 (d; 1H; J = 6 Hz); 9.9 (s; 1H) |
| 40 | 2-Hydroxy-2-methyl-octanoic acid (2-bromo-pyridin-4-yl)-amide | Pyruvic acid | 2-Bromo-pyridin-4-ylamine | Magnesium hexyl bromide | oil | (DMSO) 0.84 (m, 3H,); 1.11-1.16 (m, 1H); 1.21-1.26 (m, 6H); 1.32 (s, 3H); 1.39-1.40 (m, 1H); 1.50-1.55 (m, 1H); 1.67-1.71 (m, 1H); 5.7 (s, 1H); 7.82 (dd, 1H, J = 1.8 Hz); 8.12 (d, 1H, J = 1.7 Hz); 8.22 (d, 1H, J = 5.6 Hz); 10.1 (s, 1H) |
| 41 | 2-Hydroxy-2,4-dimethyl-pentanoic acid (2-bromo-6- | Pyruvic acid | 2-Bromo-6-methoxy-pyridin-4-ylamine | Magnesium isobutyl chloride | 103 | (DMSO) 0.77 (d, 3H, J = 6.4 Hz); 0.89 (d, 3H, J = 6.5 Hz); 1.31 (s, |

TABLE 1-continued

| Cmpd. No. | Chemical Name | Initial Product 1 | Initial Product 2 | Initial Product 3 | Melting point (° C.) | $^1$H NMR 400 Mhz |
|---|---|---|---|---|---|---|
| | methoxy-pyridin-4-yl)-amide | | | | | 3H); 1.45-1.5 (m, 1H); 1.66-1.71 (m, 2H); 3.8 (s, 3H); 5.7 (s, 1H); 7.33 (d, 1H, J = 1.4 Hz); 7.74 (d, 1H, J = 1.4 Hz); 10.1 (s, 1H) |
| 42 | 2-Hydroxy-2-methyl-hexanoic acid (2-bromo-6-methyl-pyridin-4-yl)-amide | Pyruvic acid | 2-Bromo-6-methyl-pyridin-4-ylamine | Magnesium n-butyl bromide | oil | (DMSO) 0.9 (t; 3H; J = 8 Hz); 1.1 (m; 1H); 1.2-1.3 (m; 2H); 1.32 (s; 3H); 1.33-1.41 (m; 1H); 1.5-1.6 (m; 1H); 1.7 (m; 1H); 2.4 (s; 3H); 5.7 (s; 1H); 7.7 (d; 1H; J = 1.4 Hz); 7.9 (d; 1H; J = 1.4 Hz)); 10.1 (s; 1H) |
| 43 | N-(2-Bromo-pyridin-4-yl)-2-hydroxy-2-methyl-4-phenyl-butyramide | Pyruvic acid | 2-Bromo-pyridin-4-ylamine | Magnesium phenethyl chloride | oil | (CDCl$_3$) 1.5 (s; 3H); 1.9 (m; 1H); 2.2-2.3 (m; 1H); 2.6 (m; 1H); 2.7 (m; 1H); 7.1 (m; 3H); 7.2 (m; 2H); 7.4 (d; 1H; J = 8 Hz); 7.8 (s; 1H); 8.2 (d; 1H; J = 8 Hz); 8.8 (s; 1H) |
| 44 | N-(2-Bromo-6-methoxy-pyridin-4-yl)-2-hydroxy-2-phenyl-propionamide | Pyruvic acid | 2-Bromo-6-methoxy-pyridin-4-ylamine | Magnesium phenyl bromide | 161 | (DMSO) 1.70 (s, 3 H), 3.78 (s, 3 H), 6.60 (s, 1H), 7.25-7.37 (m, 4 H), 7.57-7.59 (m, 2 H), 7.71 (d, 1 H, J = 1.5 Hz). |
| 45 | 2-Hydroxy-2-methyl-hexanoic acid (2-bromo-pyridin-4-yl)-amide | Pyruvic acid | 2-Bromo-pyridin-4-ylamine | Magnesium butyl chloride | oil | (DMSO) 0.84 (t, 3H, J = 7.1 Hz); 1.05-1.2 (m, 1H); 1.21-1.27 (m, 2H); 1.32 (s, 3H); 1.4-1.5 (m, 1H); 1.5-1.55 (m, 1H); 1.7-1.75 (m, 1H); 5.7 (s, 1H); 7.82 (dd, 1H, J = 1.8 Hz); 8.13 (d, 1H, J = 1.7 Hz); 8.22 (d, 1H, J = 5.6 Hz); 10.2 (s, 1H) |
| 46 | 2-Ethyl-2-hydroxy-pentanoic acid (2-bromo-pyridin-4-yl)-amide | Keto butyric acid | 2-Bromo-pyridin-4-ylamine | Magnesium propyl bromide | oil | (DMSO) 0.78-0.85 (m, 6H); 1.05-1.15 (m, 1H) 1.4-1.6 (m, 3H); 1.7-1.8 (m, 2H); 5.5 (s, 1H); 7.82 (dd, 1H, J = 1.8 Hz); 8.13 (d, 1H, J = 1.7 Hz); 8.22 (q, 1H, J = 5.6 Hz); 10.0 (s, 1H) |
| 47 | N-(2-Bromo-pyridin-4-yl)-2-(4-fluoro-phenyl)-2-hydroxy-butyramide | Keto butyric acid | 2-Bromo-pyridin-4-ylamine | Magnesium 4-fluoro-phenyl bromide | 55 | (DMSO) 0.79 (t, 3H, J = 7.2 Hz); 1.95-2.05 (m, 1H); 2.2-2.3 (m, 1H); 6.5 (s, 1H); 7.17 (t, 2H, J = 1.9 Hz); 7.60-7.63 (m, 2H); 7.8 (dd, 1H, J = 1.8 Hz); 8.1 (d, 1H, J = 1.7 Hz); 8.2 (d, 1H, J = 5.6 Hz); 10.4 (s, 1H) |

TABLE 1-continued

| Cmpd. No. | Chemical Name | Initial Product 1 | Initial Product 2 | Initial Product 3 | Melting point (° C.) | $^1$H NMR 400 Mhz |
|---|---|---|---|---|---|---|
| 48 | 2-Ethyl-2-hydroxy-4-methyl-pentanoic acid (2-bromo-pyridin-4-yl)-amide | Keto butyric acid | 2-Bromo-pyridin-4-ylamine | Magnesium isopropyl bromide | oil | (DMSO) 0.7-0.8 (m, 6H); 0.91 (d, 3H, J = 6.4 Hz); 1.45-1.6 (m, 2H); 1.7-1.8 (m, 3H); 5.45 (s, 1H); 7.8 (dd, 1H, J = 1.8 Hz); 8.1 (d, 1H, J = 1.7 Hz); 8.2 (d, 1H, J = 5.6 Hz); 10.1 (s, 1H) |
| 49 | 2-Ethyl-2-hydroxy-hexanoic acid (2-bromo-pyridin-4-yl)-amide | Keto butyric acid | 2-Bromo-pyridin-4-ylamine | Magnesium n-butyl chloride | oil | (DMSO) 0.80-0.85 (m, 6H); 1.03-1.09 (m, 1H); 1.18-1.26 (m, 2H); 1.39-1.45 (m, 1H); 1.48-1.58 (m, 2H); 1.69-1.78 (m, 2H); 5.48 (s, 1H); 7.82 (dd, 1H, J = 1.8 Hz); 8.14 (d, 1H, J = 1.7 Hz); 8.21 (d, 1H, J = 5.6 Hz); 10.1 (s, 1H) |
| 50 | 2-Hydroxy-2-methyl-pentanoic acid (2-trifluoromethyl-pyridin-4-yl)-amide | Pyruvic acid | 2-Trifluoromethyl-pyridin-4-ylamine | Magnesium propyl chloride | 98 | (CHCl$_3$) 0.93-0.96 (t, 3 H, J = 7.3 Hz), 1.26-1.32 (m, 1 H), 1.48-1.56 (m, 1H), 1.54 (s, 3 H), 1.62-1.69 (m, 1H), 1.93-2.01 (m, 1 H), 2.55 (s, 1 H), 7.73-7.75 (dd, 1 H, J = 5.5. 2.1 Hz), 7.99 (d, 1 H, J = 2.1 Hz), 8.62 (d, 1 H, J = 5.5 Hz), 9.11 |
| 51 | N-(2-Bromo-pyridin-4-yl)-2-cyclopentyl-2-hydroxy-butyramide | Keto butyric acid | 2-Bromo-pyridin-4-ylamine | Magnesium cyclopentyl bromide | oil | (DMSO) 0.79 (t, 3H, J = 7.4 Hz); 1.42-1.47 (m, 9H); 1.75-1.85 (m, 1H); 2.2-2.3 (m, 1H); 5.35 (s, 1H); 7.82 (dd, 1H, J = 1.8 Hz); 8.13 (d, 1H, J = 1.7 Hz); 8.21 (d, 1H, J = 5.6 Hz); 10.1 (s, 1H) |

Synthesis 52

2-Ethyl-2,6-dihydroxy-hexanoic acid (2-bromo-pyridin-4-yl)-amide (Compound 52)

Preparation According to Scheme 1, Method 1a.
Step 52.1:
6-(tert-Butyl-dimethyl-silanyloxy)-2-ethyl-2-hydroxy-hexanoic acid (2-bromo-pyridin-4-yl)-amide 9.3 mL (4.65 mmol, 3 eq) of an 0.5 M solution of 4-(tert-butyldimethylsiloxy)butyl magnesium chloride in tetrahydrofuran were added drop-by-drop to a solution cooled to 0° C. of 400 mg (1.55 mmol, 1 eq) of N-(2-bromo-pyridin-4-yl)-2-oxo-butyramide (prepared according to Synthesis 1) in 20 mL of tetrahydrofuran. After 30 minutes, the reaction medium was dry concentrated and the residue was dissolved in 30 mL of ethyl acetate and then washed with an aqueous solution saturated in ammonium chloride, and then with water. The organic phase was then dried over sodium sulphate and then dry concentrated under vacuum. The residue was purified by chromatography on silica and eluted with a 1/1 (v/v) heptane/ethyl acetate mixture. 6-(tert-Butyl-dimethyl-silanyloxy)-2-ethyl-2-hydroxy-hexanoic acid (2-bromo-pyridin-4-yl)-amide was obtained in the form of a colourless oil.

Step 52.2:
2-Ethyl-2,6-dihydroxy-hexanoic acid (2-bromo-pyridin-4-yl)-amide 1 mL (1 mmol, 1.1 eq) of ammonium tetrabutyl fluoride as a 1 M solution in tetrahydrofuran was added to a solution of 410 mg (0.92 mmol, 1 eq) of 6-(tert-butyl-dimethyl-silanyloxy)-2-ethyl-2-hydroxy-hexanoic acid (2-bromo-pyridin-4-yl)-amide in 20 mL of tetrahydrofuran. The solution was agitated at ambient temperature for 16 hours and then dry concentrated. The residue was dissolved in ethyl acetate and this solution was washed with an aqueous solution saturated in ammonium chloride and then with water. The organic phase was dried on sodium sulphate and then dry concentrated under vacuum. The residue was purified by chromatography on silica and eluted by a 1/1

(v/v) heptane/ethyl acetate mixture, and then with 100% ethyl acetate. 2-ethyl-2,6-dihydroxy-hexanoic acid (2-bromo-pyridin-4-yl)-amide was obtained in the form of a white solid.

Melting point=103° C. NMR ($^1$H, DMSO): 0.78-0.82 (t, 3 H, J=7.4 Hz), 1.03-1.15 (m, 1 H), 1.34-1.37 (m, 2 H), 1.49-1.58 (m, 3 H), 1.73-1.76 (m, 2 H), 3.32-3.36 (m, 2H), 4.32-4.34 (t, 1 H, J=5.1 Hz), 5.48 (s, 1 H), 7.81-7.83 (dd, 1 H, J=5.7, 1.9 Hz), 8.14 (d, 1 H, J=1.9 Hz), 8.22 (d, 1 H, J=5.7 Hz), 10.10 (s, 1 H).

Synthesis 53

2-Hydroxy-2,4-dimethyl-pentanoic acid (2-cyano-6-methoxy-pyridin-4-yl)-amide (Compound 53)

In a 6 mL microwave tube, 0.2 g (0.6 mmol, 1 eq) of 2-hydroxy-2,4-dimethyl-pentanoic acid (2-bromo-6-methoxy-pyridin-4-yl)-amide (Synthesis 41) was dissolved in 5 mL of dimethylformamide and 0.054 g (0.6 mmol, 1 eq) of copper (I) cyanide then added. The reaction mixture was then degassed under vacuum, and then 0.035 g (0.03 mmol, 0.05 eq) of palladium tetrakis triphenylphosphine was added. The tube was sealed and heated for 1 hour at 170° C. in a microwave oven. The reaction mixture was then diluted with 50 mL of ethyl acetate, and then filtered on celite; the filtrate was washed three times with 50 mL of water, then dried on magnesium sulphate, and dry concentrated under vacuum. The residue was purified by chromatography on silica in eluting using a 7/3 (v/v) heptane/ethyl acetate mixture. The product obtained was again purified by chromatography on silica by eluting with a 99/1 (v/v) dichloromethane/methanol mixture. 2-Hydroxy-2,4-dimethyl-pentanoic acid (2-cyano-6-methoxy-pyridin-4-yl)-amide is obtained in the form of an oil.

NMR ($^1$H, DMSO): 0.67 (m,3H); 0.8 (m, 3H); 1.23 (s, 3H), 1.35-1.45 (m, 1H); 1.6-1.7 (m, 2H); 3.76 (s, 3H); 5.68 (s, 1H); 7.54 (d, 1H, J=1.6 Hz); 7.92 (d, 1H, J=1.6 Hz); 10.2 (s,H).

Synthesis 54

N-(2-Bromo-6-methoxy-pyridin-4-yl)-2-hydroxy-propionamide (Compound 54)

Under the conditions of preparation of N-(2-bromo-6-methoxy-pyridin-4-yl)-2-cyclopentyl-2-hydroxy-propionamide (Synthesis 21) described in Method 1a above, N-(2-bromo-6-methoxy-pyridin-4-yl)-2-hydroxy-propionamide was also obtained as a secondary product of the reaction in the form of a white solid.

NMR ($^1$H, DMSO): 1.3 (d; 3H; J=8 Hz); 3.8 (s; 3H); 4.1-4.2 (q; 1H; J1=7 Hz; J2'=7 Hz); 7.3 (d; 1H; J=1.4 Hz); 7.7 (d; 1H; J=1.4 Hz); 10.2 (s; 1H).

Synthesis 55

N-(2-Bromo-6-methoxy-pyridin-4-yl)-2-hydroxy-butyramide (Compound 55)

Under the conditions of preparation of N-(2-bromo-6-methoxy-pyridin-4-yl)-2-cyclopentyl-2-hydroxy-butyramide (Synthesis 9) described in Method 1a above, N-(2-bromo-6-methoxy-pyridin-4-yl)-2-hydroxy-butyramide was also obtained as a secondary product of the reaction in the form of a white solid.

NMR ($^1$H, DMSO): 0.9 (Tr; 3H; J=8 Hz); 1.6 (m; 1H); 1.7 (m; 1H); 3.8 (s; 3H); 4.0 (m; 1H); 5.9 (s; 1H); 7.3 (d; 1H; J=1.6 Hz); 7.7 (d; 1H; J=1.6 Hz); 10.2 (s; 1H).

Synthesis 56

N-(2-Bromo-6-methoxy-pyrimidin-4-yl)-2-ethyl-2-hydroxy-butyramide (Compound 56)

179 mg (0.59 mmol, 1 eq) of N-(2-bromo-6-methoxy-pyrimidin-4-yl)-oxalamic acid ethyl ester were dissolved in 5 mL of tetrahydrofuran. 0.59 mL (1.77 mmol, 3 eq) of a solution of magnesium ethyl bromide (3 M) in tetrahydrofuran was added drop-by-drop at 0° C. After 30 minutes, 5 mL of a solution of hydrochloric acid (1 M) and 50 mL of ethyl acetate were added. The organic phase was washed with 2×50 mL of water, and then dried over magnesium sulphate and dry concentrated under vacuum. The residue was purified by chromatography on silica eluting with a 1/1 (v/v) heptane/ethyl mixture. N-(2-Bromo-6-methoxy-pyrimidin-4-yl)-2-ethyl-2-hydroxy-butyramide was obtained in the form of a white solid.

NMR ($^1$H, DMSO): 0.8 (t; 6H; J=8 Hz); 1.6 (m; 2H); 1.7-1.8 (m; 2H); 3.9 (s; 3H); 5.8 (s; 1H); 8.0 (s; 1H); 9.7 (s; 1H).

Preparation of N-(2-Bromo-6-methoxy-pyrimidin-4-yl)-oxalamic acid ethyl ester:

120 mg (0.59 mmol, 1 eq) of 2-bromo-6-methoxy-pyrimidin-4-ylamine was dissolved in 10 mL of dichloromethane at 0° C. 0.9 mL (0.65 mmol, 1.1 eq) of triethylamine and 80.3 mg (0.59 mmol, 1 eq) of ethyl oxalate chloride were added. After 30 minutes, at ambient temperature, 30 mL of dichloromethane was added. The organic phase was then washed with 50 mL of a saturated aqueous sodium bicarbonate solution, and then with 2×50 mL of water. The organic phase was then isolated and dried over magnesium sulphate, and then dry concentrated under vacuum. N-(2-Bromo-6-methoxy-pyrimidin-4-yl)-oxalamic acid ethyl ester was obtained in the form of a pale yellow oil.

Preparation of 2-Bromo-6-methoxy-pyrimidin-4-ylamine:

85 mL (34 mmol, 2.2 eq) of an ammonia solution (0.4 M) in tetrahydrofuran was added to 5 mg (0.32 mmol, 1 eq) of 2,4,6-tribromo-pyrimidine in a 250 mL flask. After 2 hours at ambient temperature, the reaction mixture was dry concentrated under vacuum. 5.4 g of a white solid was obtained. 2.5 g of this solid were then mixed with 650 mg of sodium hydroxide in 8 mL of methanol. The mixture was heated to 100° C. in a microwave oven for 2 hours. The reaction mixture was then diluted with 100 mL of ethyl acetate, and then washed with 2×50 mL of water. The organic phase was then dried over magnesium sulphate and dry concentrated under vacuum. The residue was purified by chromatography on silica by eluting with a 1/1 (v/v) heptane/ethyl acetate mixture. 2-Bromo-6-methoxy-pyrimidin-4-ylamine was obtained in the form of a white solid.

Synthesis 57

1-Hydroxy-cyclopentanecarboxylic acid (2-bromo-pyridin-4-yl)-amide (Compound 57)

Preparation According to Scheme 1, Method 1b:

2.2 mL (25.9 mmol, 9 eq) of oxalyl chloride were added, drop-by-drop, to a solution, cooled to 0° C., of 1.13 g (8.7 mmol, 3 eq) of 1-hydroxy-cyclopentanecarboxylic acid in 20 mL of tetrahydrofuran. The solution was agitated at 0° C.

for 1 hour, and then at ambient temperature for 16 hours. The reaction mixture was evaporated dry. The residue was absorbed in dichloromethane and added to a solution of 500 mg (2.80 mmol, 1 eq) of 5-bromo-pyridin-3-ylamine in 20 ml of dichloromethane. 1.2 mL (8.6 mmol, 3 eq) of triethylamine was then added. The mixture was agitated at ambient temperature for 30 minutes. No initial product remained. The reaction mixture was poured into a frozen mixture of sodium and dichloromethane. The organic phase was extracted in dichloromethane and then washed in water twice, then dried over sodium sulphate, and dry concentrated under vacuum. The residue was precipitated in dichloromethane and heptanes. 1-hydroxy-cyclopentanecarboxylic acid (2-bromo-pyridin-4-yl)-amide was obtained in the form of a white solid.

Melting point=153° C. NMR ($^1$H, DMSO): 1.70-1.76 (m, 6 H), 1.95-2.03 (m, 2 H), 5.74 (s, 1 H), 7.81-7.83 (dd, 1 H, J=5.7, 1.9 Hz), 8.14 (d, 1 H, J=1.8 Hz), 8.23 (d, 1 H, J=5.7 Hz), 10.35 (s, 1H).

Synthesis 58

1-Hydroxy-cyclohexanecarboxylic acid (2-bromo-pyridin-4-yl)-amide (Compound 58)

Prepared in the same way as Synthesis 57, by replacing 1-hydroxycyclopentane carboxylic acid with 1-hydroxy-cyclohexane carboxylic acid. 1-Hydroxy-cyclohexane carboxylic acid (2-bromo-pyridin-4-yl)-amide was obtained in the form of a white solid.

Melting point=179° C. NMR ($^1$H, DMSO) 1.15-1.28 (m, 1 H), 1.50-1.71 (m, 9 H), 5.61 (s, 1 H), 7.79-7.81 (dd, 1 H, J=5.7, 1.9 Hz), 8.12 (d, 1 H, J=1.8 Hz), 8.22 (d, 1 H, J=5.7 Hz), 10.31 (1 H, s).

Synthesis 59

4-(2-Hydroxy-2-methyl-pentanoylamino)-pyridine-2-carboxylic acid methyl ester (Compound 59)

Preparation According to Scheme 1, Method 1c:
377 mg (2.3 mmol 1.4 eq) of 1,2,4-triazole was added to a solution of 220 mg (1.66 mmol, 1 eq) of 2-hydroxy-2-methyl-pentanoic acid in 20 mL of dichloromethane. This solution was agitated for 2 hours at ambient temperature. The suspension was cooled to 0° C. and the N-sulfinyl 4-pyridinamine 2-carboxylic methyl ester was added. The medium was agitated for 3 hours at 0° C., then at ambient temperature for 16 hours. The precipitate was filtered and the filtrate was washed with water and acidified with hydrochloric acid up to pH 1, and then washed in water with water. The aqueous phase was extracted with dichloromethane and the organic phase was then dried over sodium sulphate and then dry concentrated under vacuum. The residue was purified by chromatography on silica gel by eluting with a 1/1 (v/v) mixture of heptanes/ethyl acetate. The residue obtained was purified again by chromatography on silica by eluting with a 2/3 (v/v) heptane/ethyl acetate mixture. 4-(2-Hydroxy-2-methyl-pentanoylamino)-pyridine-2-carboxylic acid methyl ester was obtained in the form of a white solid.

Melting point=122° C. NMR ($^1$H, DMSO) 0.93-0.97 (t, 3 H, J=7.3 Hz), 1.25-1.38 (m, 1 H), 1.45-1.54 (m, 1 H), 1.55 (s, 3 H), 1.62-1.69 (m, 1 H), 1.95-1.98 (m, 1 H), 2.35 (s, 1 H), 4.02 (s, 3 H), 7.98-8.0 (dd, 1 H, J=5.5, 2.2 Hz), 8.18 (d, 1 H, J=2.1 Hz), 8.66 (d, 1 H, J=5.5 Hz), 9.06 (s, 1 H).

Preparation of N-sulfinyl 4-Pyridinamine 2-carboxylic methyl ester:
800 µL (11 mmol, 4.8 eq) of thionyl chloride was added to a solution cooled to −10° C. of 320 mg (4.7 mmol, 2 eq) of imidazole in 30 mL of dichloromethane. This solution was agitated for 10 minutes at ambient temperature. The imidazolium chloride was then filtered. 800 µL (11 mmol, 4.8 eq) of thionyl chloride was added to the filtrate at −10° C. and this new solution was agitated for 10 minutes at ambient temperature. This solution was added at −40° C. to 350 mg (2.3 mmol, 1 eq) of 4-amino-pyridine-2-carboxylic acid methyl ester in 20 mL of dichloromethane. This new solution was agitated at ambient temperature for 2 hours. The precipitate was then filtered and the filtrate was dry evaporated. The oily residue is used as is.

Preparation of 2-hydroxy-2-methyl-pentanoic acid:
Preparation According to Scheme 3:
In a 50 mL three-collar flask, 2 g (22.71 mmol, 1 eq) of pyruvic acid was dissolved in 10 ml of tetrahydrofuran and the solution was cooled to −10° C. 34.1 mL (68.14 mmol, 3 eq) of a propyl magnesium bromide solution (2 M) in tetrahydrofuran were added drop-by-drop and the reaction mixture was left under agitation for 2 hours at −10° C. 50 mL of an aqueous solution of propyl magnesium bromide (2 M) in tetrahydrofuran were added drop-by-drop and the reaction mixture was left to agitate for 2 hours at −10° C. 50 mL of an aqueous solution of hydrochloric acid (1 M) were then added and the organic phase was extracted with 2×50 mL ethyl acetate, and then dried over magnesium sulphate and dry concentrated under vacuum. The 2-hydroxy-2-methyl-pentanoic acid was then obtained in the form of a slightly pale yellow oil.

Synthesis 60

2-Hydroxy-2-methyl-pentanoic acid (2-bromo-6-methoxy-pyridin-4-yl)-amide (Compound 60)

Preparation According to Scheme 1, Method 1c:
In a 50 mL single collar flask 500 mg (2.4 mmol, 1 eq) of 2 bromo-6-methoxy-pyridin-4-ylamine were introduced, to which was added 20 mL of toluene and 586 mg (4.92 mmol, 2 eq) of thionyl chloride, and the mixture heated at reflux for 3 hours. The reaction medium was dry concentrated under vacuum, and the residue was returned to solution in 20 mL of acetonitrile. 325 mg (2.46 mmol, 1 eq) of 2-hydroxy-2-methyl-pentanoic acid was then added at ambient temperature. After 16 hours at ambient temperature, the reaction mixture was heated to 80° C. for 4 hours, then to 60° C. for 3 days, and the reaction mixture was then dry concentrated. The residue was dissolved in 50 mL ethyl acetate. The solution was washed twice with 50 mL of an aqueous solution saturated with ammonium chloride, and then twice with 50 mL of water. The organic phase was then dried over magnesium sulphate and then dry concentrated under vacuum. A brown oil was obtained which was purified by chromatography on silica with a 1/1 (v/v) heptane/ethyl acetate mixture as the eluent. A brown solid was then obtained and purified by chromatography on grafted C18 silica with a water/acetonitrile mixture as the eluent (gradient 5 at 100% acetonitrile). 2-Hydroxy-2-methyl-pentanoic acid (2-bromo-6-methoxy-pyridin-4-yl)-amide was obtained in the form of a white solid.

Melting point=122° C. NMR ($^1$H, DMSO): 0.9 (t; 3H; J=4 Hz); 1.1-1.3 (m; 1H); 1.4 (s; 3H); 1.4-1.5 (m; 1H); 1.6 (m; 1H); 1.7 (m; 1H); 3.9 (s; 3H); 5.8 (s; 1H); 7.4 (d; 1H; J=1.4 Hz); 7.8 (d; 1H; J=1.4 Hz); 10.2 (s; 1H).

Synthesis 61

2-Hydroxy-2-methyl-pentanoic acid (6-bromo-2-oxo-1,2-dihydro-pyridin-4-yl)-amide (Compound 61)

2 drops of hydrobromic acid at 45% in acetic acid were added to a solution of 100 mg (0.31 mmol, 1 eq) of 2-hydroxy-2-methyl-pentanoic acid (2-bromo-6-methoxy-pyridin-4-yl)-amide (Synthesis 60) in 5 mL of acetic acid. This solution was heated at reflux for 6 hours. The solvent was evaporated and the residue was absorbed by ethyl acetate and washed with water. The extracted phase was extracted with ethyl acetate. The organic phases were collected and dried over sodium sulphate. The residue was purified on silica gel and eluted by a 7/3 (v/v) heptane/ethyl acetate mixture. 2-hydroxy-2-methyl-pentanoic acid (6-bromo-2-oxo-1,2-dihydro-pyridin-4-yl)-amide was obtained in the form of a white solid.

Melting point=188° C. NMR ($^1$H, DMSO) 0.82-0.85 (t, 3 H, J=7.3 Hz), 1.12-1.15 (m, 1H), 1.30 (s, 3 H), 1.39-1.54 (m, 2H), 1.63-1.66 (m, 1 H), 5.69 (s, 1 H), 7.11 (s, 1 H), 7.51 (s, 1 H), 9.96 (s, 1 H).

Synthesis 62

N-(2-Bromo-6-methoxy-pyridin-4-yl)-2-hydroxy-2-methyl-butyramide (Compound 62)

Preparation According to Scheme 1, Method 1c:

2-Hydroxy-hexanoic acid (2-bromo-6-methoxy-pyridin-4-yl)-amide was prepared according to the procedure described in Synthesis 6 by replacing 2-hydroxy-2-methyl-pentanoic acid by 2-hydroxy-2-methyl-butyric acid. N-(2-Bromo-6-methoxy-pyridin-4-yl)-2-hydroxy-2-methyl-butyramide was obtained in the form of a white solid.

NMR ($^1$H, DMSO): 0.8 (t; 3H; J=8 Hz); 1.3 (s; 3H); 1.6 (m; 1H); 1.7 (m; 1H); 3.81 (s; 3H); 5.7 (s; 1H); 7.3 (d; 1H; J=1.5 Hz); 7.7 (d; 1H; J=1.4 Hz); 10.1 (s; 1H).

Synthesis 63

2-Hydroxy-hexanoic acid (2-bromo-6-methoxy-pyridin-4-yl)-amide (Compound 63)

Preparation According to Scheme 1, Method 1c:

2-Hydroxy-hexanoic acid (2-bromo-6-methoxy-pyridin-4-yl)-amide was prepared according to the procedure described in Synthesis 60 by replacing 2-hydroxy-2-methyl-pentanoic acid by 2-hydroxy-hexanoic acid. 2-Hydroxy-hexanoic acid (2-bromo-6-methoxy-pyridin-4-yl)-amide was obtained in the form of a colourless oil.

NMR (1H, DMSO): 0.9 (t; 3H; J=8 Hz); 1.3 (m; 4H); 1.5-1.6 (m; 1H); 1.6-1.7 (m; 1H); 3.8 (s; 3H); 4.0-4.1 (m; 1H); 5.9 (s; 1H); 7.3 (d; 1H; J=1.4 Hz); 7.7 (d; 1H; J=1.5 Hz); 10.2 (s; 1H).

Synthesis 64

2-Hydroxy-2-isopropyl-pentanoic acid (2-bromo-6-methoxy-pyridin-4-yl)-amide (Compound 64)

Preparation According to Scheme 2, Method 1d:
Step 64.1:
N-(2-Bromo-6-methoxy-pyridin-4-yl)-oxalamic acid ethyl ester In a 250 mL three-collar flask under nitrogen, and at ambient temperature, 10 g (49.25 mmol, 1 eq) of 2-bromo-6-methoxy-pyridine-4-ylamine (initial product 1) were partially dissolved in 100 mL of dichloromethane. The reaction mixture was cooled to 0° C., and then 7.51 mL (54.18 mmol, 1.1 eq) of triethylamine were added, followed by 5.50 mL (49.25 mmol, 1 eq) of ethyl oxalate chloride drop-by-drop. After 1 hour at ambient temperature, 250 mL of water was added followed by 150 mL of dichloromethane. The organic phase was then extracted and washed twice with 150 mL of an aqueous solution saturated with sodium bicarbonate, then with 150 mL of an aqueous solution saturated with ammonium chloride, and then twice with water. After drying over magnesium sulphate, the organic phase was concentrated under vacuum and the residue was triturated in diethyl ether. N-(2-Bromo-6-methoxy-pyridin-4-yl)-oxalamic acid ethyl ester was isolated in the form of a pinkish white solid.

Step 64.2:
N-(2-Bromo-6-methoxy-pyridin-4-yl)-oxalamic acid

In a 500 mL three collar flask under nitrogen and at ambient temperature, 6.70 g (22.10 mmol, 1 eq) of N-(2-bromo-6-methoxy-pyridin-4-yl)-oxalamic acid ethyl ester (22.10 mmol, 1 eq) was dissolved in a mixture of 210 mL of tetrahydrofuran and 23 mL of methanol. 4.42 g (110.52 mmol, 5 eq) of sodium hydroxide was added at −20° C. under agitation. After 1 hour at −10° C., the reaction mixture was poured into 200 mL of water and approximately 9 mL of aqueous hydrochloric acid (12 N) was added up to pH 2. The organic phase was extracted with 250 mL of ethyl acetate, dried over magnesium sulphate and dry concentrated under vacuum. The white solid residue was triturated in diethyl ether. N-(2-Bromo-6-methoxy-pyridin-4-yl)-oxalamic acid was isolated in the form of a white solid.

Step 64.3:
N-(2-Bromo-6-methoxy-pyridin-4-yl)-N'-methoxy-N'-methyl-oxalamide

In a 500 mL three collar flask under nitrogen, and at ambient temperature, 11.60 g (42.17 mmol, 1 eq) of N-(2-bromo-6-methoxy-pyridin-4-yl)-oxalamic acid was suspended in 400 mL of tetrahydrofuran, and then 1354 g (42.17 mmol, 1 eq) of tetrafluoroborate of 2-(1H-benzotriazol-1-yl)-1, 1,3,3-tetramethyluronium was added. After 30 minutes at ambient temperature, 21.77 mL (126.51 mmol, 3 eq) of N,N-diisopropylethylamine and 4.11 g (42.17 mmol, 1 eq) of chlorohydrate of N,O-dimethylhydroxylamine were added. After 3 hours and 30 minutes of agitation at ambient temperature, the reaction mixture was poured into 400 mL of aqueous citric acid at 5%. 400 mL of ethyl acetate was added and the organic phase was extracted and then washed with 300 mL of an aqueous solution saturated with sodium bicarbonate and twice with 300 mL of water, and then dried over magnesium sulphate. After dry concentration under vacuum, N-(2-bromo-6-methoxy-pyridin-4-yl)-N'-methoxy-N'-methyl-oxalamide acid was isolated in the form of a white solid.

Step 64.4:
N-(2-Bromo-6-methoxy-pyridin-4-yl)-3-methyl-2-oxo-butyramide

In a 100 mL three collar flask under nitrogen, and at ambient temperature, 2.5 g (7.86 mmol, 1 eq) of N-(2-bromo-6-methoxy-pyridin-4-yl)-N'-methoxy-N'-methyl-oxalamide was dissolved in 75 mL of tetrahydrofuran. The reaction mixture was cooled to −15° C., and then 7.86 mL (23.58 mmol, 3 eq) of a solution of magnesium dipropyl chloride (initial product 2) (3 M) was then added to the tetrahydrofuran. After 30 minutes under agitation at 0°, the reaction mixture was treated with 200 mL of an aqueous solution saturated with ammonium chloride. The organic phase was extracted with 200 mL of ethyl acetate, then washed twice with 100 mL of water, then dried over magnesium sulphate, and dry concentrated under vacuum. The residue obtained was chromatographed on silica by eluting with a 9/1 (v/v) heptane/ethyl acetate mixture. N-(2-Bromo-6-methoxy-pyridin-4-yl)-3-methyl-2-oxo-butyramide was isolated in the form of a white solid.

Step 64.5:
2-Hydroxy-2-isopropyl-pentanoic acid (2-bromo-6-methoxy-pyridin-4-yl)-amide In a 50 mL three collar flask under nitrogen and at ambient temperature, 0.45 g (1.49 mmol, 1 eq) of N-(2-bromo-6-methoxy-pyridin-4-yl)-3-methyl-2-oxo-butyramide was dissolved in 13.5 mL of tetrahydrofuran. The reaction mixture was cooled to −20° C., and then 2.24 mL (4.48 mmol, 3 eq) of a magnesium n-propyl bromide solution (2 M) was added quickly (initial product 3) was added quickly to the tetrahydrofuran. After 10 minutes under agitation at −10°, the reaction mixture was poured into 30 mL of an aqueous solution saturated with ammonium chloride. The organic phase was extracted with 30 mL of ethyl acetate, washed with 30 mL of water, and then dried over magnesium sulphate. The residue was chromatographed on a silica column by eluting with a 9/1 (v/v) heptane/ethyl acetate mixture. A product was recovered in the form of an oil which was triturated with diisopropyl ether and heptanes. 2-Hydroxy-2-isopropyl-pentanoic acid (2-bromo-6-methoxy-pyridin-4-yl)-amide was isolated in the form of a white solid.

Melting point=116° C. NMR ($^1$H, DMSO): 0.78-0.88 (m. 6H); 1.03 (m, 1H); 1.4-1.7 (m, 3H); 1.94 (m; 1H); 3.8 (s, 3H); 5.33 (s, 1H); 7.33 (d, J=1.4 Hz, 1H); 7.73 (d, J=1.4 Hz, 1H); 9.9 (s, 1H).

Syntheses 65 to 70

Syntheses 65 to 70 are described in table 1 below.

The compounds were synthesised according to the above procedure by replacing the initial products 1, 2 and 3 mentioned in Synthesis 64 by the initial products mentioned in Table 2. In the context of the $^1$H NMR data shown in Table 2, s=singlet, d=doublet, t=triplet, m=multiplet, q=quartet, J=coupling constant in hertz (Hz).

TABLE 2

| Cmpd. # | Chemical Name | Initial Product 1 | Initial Product 2 | Initial Product 3 | Melting point (° C.) | $^1$H NMR 400 Mhz |
|---|---|---|---|---|---|---|
| 65 | 2-Hydroxy-2-isopropyl-pentanoic acid (2-bromo-6-methoxy-pyridin-4-yl)-amide | 2-Bromo-6-methoxy-pyridin-4-ylamine | Magnesium isopropyl bromide | Magnesium sec-propyl bromide | 116 | (DMSO) 0.78-0.88 (m, 6H); 1.0-1.1 (m, 1H); 1.4-1.5 (m, 1H); 1.5-1.6 (m, 1H), 1.6-1.7 (m, 1H); 1.9-2.0 (m, 1H); 3.8 (s, 3H); 5.33 (s, 1H); 7.33 (d, 1H, J = 1.4 Hz); 7.73 (d, 1H, J = 1.4 Hz); 9.9 (s, 1H) |
| 66 | 2-Butyl-2-hydroxy-hexanoic acid (2-bromo-6-methoxy-pyridin-4-yl)-amide | 2-Bromo-6-6-methoxy-pyridin-4-ylamine | Magnesium n-butyl bromide | Magnesium n-butyl bromide | oil | (DMSO) 0.9 (t; 6H; J = 8 Hz); 1.0-1.1 (m; 2H); 1.2 (m; 4H); 1.3-1.4 (m; 2H); 1.5-1.6 (m; 2H); 1.7-1.8 (m; 2H); 3.8 (s; 3H); 5.5 (s; 1H); 7.3 (d; 1H; J = 1.4 Hz); 7.7 (d; 1H; J = 1.4 Hz); 10.0 (s; 1H) |
| 67 | N-(2-Bromo-6-methoxy-pyridin-4-yl)-2,2-dicyclopentyl-2-hydroxy-acetamide | 2-Bromo-6-methoxy-pyridin-4-ylamine | Magnesium cyclopentyl bromide | Magnesium cyclopentyl bromide | 162 | (DMSO) 1.31-1.58 (m, 14H); 1.66-1.67 (m, 2H); 2.24-2.28 (m, 2H); 3.8 (s, 3H); 5.32 (s, 1H); 7.31 (d, 1H, J = 1.4 Hz); 7.72 (d, 1H, J = 1.4 Hz); 9.9 (s, 1H) |
| 68 | N-(2-Bromo-6-methoxy-pyridin-4-yl)-2-hydroxy-2-isopropyl-3-methyl-butyramide | 2-Bromo-6-methoxy-pyridin-4-ylamine | Magnesium isopropyl bromide | Magnesium isopropyl bromide | 123 | (DMSO) 0.86 (m, 12H); 2.08 (m, 2H); 3.8 (s, 1H); 5.21 (s, 1H); 7.33 (d, 1H, J = 1.4 Hz); 7.74 (d, 1H, J = 1.4 Hz); 9.9 (s, 1H) |

TABLE 2-continued

| Cmpd. # | Chemical Name | Initial Product 1 | Initial Product 2 | Initial Product 3 | Melting point (° C.) | $^1$H NMR 400 Mhz |
|---|---|---|---|---|---|---|
| 69 | N-(2-Bromo-6-methoxy-pyridin-4-yl)-2-hydroxy-2-(tetrahydro-pyran-4-yl)-propionamide | 2-Bromo-6-methoxy-pyridin-4-ylamine | Magnesium tetrahydropyran-4-yl chloride | Magnesium methyl bromide | 140 | (DMSO) 1.22-1.1.35 (m, 5H); 1.46-1.58 (m, 2H); 1.8-1.9 (m, 1H); 3.16-3.28 (m, 2H); 3.8-3.84 (m, 3H); 3.87-3.91 (m, 2H); 5.75 (s, 1H); 7.33 (d, 1H, J = 1.3 Hz); 7.74 (d, 1H, J = 1.4 Hz); 10.1 (s, 1H) |
| 70 | 2-Hydroxy-2-propyl-hexanoic acid (2-bromo 6-methoxy-pyridin-4-yl)-amide | 2-Bromo-6-o-methoxy-pyridin-4-ylamine | Magnesium butyl bromide | Magnesium propyl bromide | oil | (DMSO) 0.8 (m; 6H); 1.0-1.1 (m; 2H); 1.2-1.3 (m; 2H); 1.4-1.6 (m; 4H); 1.6-1.8 (m; 2H); 3.8 (s; 3H); 5.5 (s; 1H); 7.3 (d; 1H; J = 1.4 Hz); 7.7 (d; 1H; J = 1.4 Hz); 10.0 (s; 1H) |

Synthesis 71

(R)-2-Hydroxy-2,4-dimethyl-pentanoic acid (2-bromo-6-methoxy-pyridin-4-yl)-amide Compound 71A (S)-2-Hydroxy-2,4-dimethyl-pentanoic acid (2-bromo-6-methoxy-pyridin-4-yl)-amide (Compound 71B)

The two enantiomers of the racemic mixture prepared in Synthesis 41 were separated by HPLC (high pressure liquid chromatography) on a chiral stationary phase Chiralpak type Ia, Chiral Technologies, diameter 2 cm, length 25 cm, eluting with 93/7 (v/v) heptane/isopropanol containing 0.1% (v/v) trifluoroacetic acid. The flow rate was 18 mL/minute. The injection volume was 1 mL of a solution of 20 mg of the racemic mixture dissolved in a 1/1 (v/v) mixture of heptane/isopropanol. The retention times of the two enantiomers were 8.38 minutes and 9.70 minutes. After 6 injections, 40 mg of the two enantiomers were obtained as oils after solvent evaporation.

Analysis 71

Further analysis was performed using chiral HPLC (Chiralpak type Ia, Chiral Technologies, 250×4, 6 mm, eluent 93/7 (v/v) heptane/isopropanol containing 0.1% (v/v) trifluoroacetic acid with a flow rate of 1 mL/minute for 20 minutes. Compound 71A had a retention time of 6.77 minutes, and Compound 71B had a retention time of 8.71 minutes.

The absolute configuration of Compound 71B was determined using X-ray diffraction (XRD), and found to be the (S) configuration. Accordingly, Compound 71A was determined to be in the (R) configuration.

Syntheses 72-80

Separation of the enantiomers in a number of racemic mixtures (obtained in earlier syntheses) was performed in the same manner as described in Synthesis 71. Analysis was done in the same manner as described in Analysis 71, with the following modifications:

| Racemic Mixture (Compound No.) | Name | Analysis elution | Compound No. | Analysis retention Time (min) |
|---|---|---|---|---|
| 8 | 2-Hydroxy-2-methyl-hexanoic acid (2-bromo-6-methoxy-pyridin-4-yl)-amide | (as in Analysis 71) | 72A 72B | 6.94 8.45 |
| 9 | N-(2-Bromo-6-methoxy-pyridin-4-yl)-2-cyclopentyl-2-hydroxy-butyramide | 92/8 (v/v) heptane/isopropanol containing 0.1% trifluoroacetic acid over 30 minutes | 73A 73B | 6.94 17.74 |
| 13 | N-(2-Bromo-6-methoxy-pyridin-4-yl)-2-ethyl-2-hydroxy-3-methyl-butyramide | 85/15 (v/v) heptane/isopropanol containing 0.1% trifluoroacetic acid over 15 minutes | 74A 74B | 4.66 5.13 |

-continued

| Racemic Mixture (Compound No.) | Name | Analysis elution | Compound No. | Analysis retention Time (min) |
|---|---|---|---|---|
| 19 | 2-Ethyl-2-hydroxy-pentanoic acid (2-bromo-6-methoxy-pyridin-4-yl)-amide | (as in Analysis 71) | 75A<br>75B | 7.23<br>9.74 |
| 25 | N-(2-Bromo-6-methoxy-pyridin-4-yl)-2-hydroxy-2,3-dimethyl-butyramide | (as in Analysis 71) | 76A<br>76B | 9.83<br>12.88 |
| 51 | N-(2-Bromo-pyridin-4-yl)-2-cyclopentyl-2-hydroxy-butyramide | 93/7 (v/v) heptane/isopropanol containing 0.1% trifluoroacetic acid over 35 minutes | 77A<br>77B | 10.26<br>28.59 |
| 60 | 2-Hydroxy-2-methyl-pentanoic acid (2-bromo-6-methoxy-pyridin-4-yl)-amide | (as in Analysis 71) | 78A<br>78B | 7.61<br>8.73 |
| 64 | 2-Hydroxy-2-isopropyl-pentanoic acid (2-bromo-6-methoxy-pyridin-4-yl)-amide | 90/10 (v/v) heptane/isopropanol containing 0.1% (v/v) trifluoroacetic acid over 30 minutes | 79A<br>79B | 6.05<br>10.86 |
| 1 | 2-Hydroxy-2-methyl-hexanoic acid (2-bromo-pyridin-4-yl)-amide | 97/3 (v/v) heptane/isopropanol containing 0.02% (v/v) trifluoroacetic acid over 50 minutes | 80A<br>80B | 32.98<br>36.50 |

Biological Studies

Study 1

The N-(pyrid-4-yl)amides and N-(pyrimidin-4-yl)amides described herein exhibit androgen receptor (AR) inhibiting properties. This AR inhibiting activity was measured in a transactivation test by the dissociation constants KdR (rest), KdA (active), and Kdapp (apparent).

A compound may be said to be an AR inhibitor if it has a dissociation constant, Kdapp, of less than or equal to 1 μM, and a KdR/KdA ratio of less than or equal to 10 in a transactivation test.

Preferred AR type receptor inhibitors have a dissociation constant of less than or equal to 500 nM, and more preferably less than or equal to 100 nM.

The transactivation test is carried out in the cell line PALM (PC3 androgen receptor Luciferase MMTV), which is a stable transfectant containing the plasmids PMMTV-neo-Luc (reporter gene) and pSG5puro-AR.

In this study, the affinity of each test compound for the 2 states of the receptor (KdR and KdA) is determined together with the apparent Kd (KdApp). This constant depends upon the 2 Kd's (KdR and KdA), but also depends on the initial equilibrium of the receptor between the active state and rest state ($L_0$) and on its expression rate. It is determined by the following formula:

$$1/KdApp = (L_0/(1+L_0)) \times (1/KdR) + (1/(1+L_0)) \times (1/KdA)$$

In order to determine these constants, "cross curves" of the test compound against a reference agonist, methyl trienolone, are carried out on a 96-well plate. The test compound is used in 10 concentrations and the reference agonist in 7 concentrations.

A Kdapp values for a number of compounds are reported in Table 3.

TABLE 3

| Compound No. | Kdapp (nM) |
|---|---|
| 1 | 75 |
| 8 | 30 |
| 23 | 15 |
| 24 | 300 |
| 32 | 100 |
| 41 | 20 |
| 43 | 100 |
| 59 | 6000 |

The following compounds were found to have a Kdapp of 10 μM or less:
Compounds 1, 8, 9, 13, 19, 23, 24, 25, 27, 32, 38, 41, 43, 51, 59, 60, 64, 66, 68, 69, 71A, 71B, 72A, 72B, 73A, 73B, 74A, 74B, 75A, 75B, 76A, 76B, 77A, 77B, 78A, 78B, 79A, 79B, 80A, and 80B.

The following compounds were found to have a Kdapp of 1 μM or less:
Compounds 1, 8, 9, 13, 19, 23, 24, 25, 27, 32, 38, 41, 43, 51, 60, 64, 66, 68, 69, 71A, 71B, 72A, 72B, 73A, 73B, 74A, 74B, 75A, 75B, 76A, 76B, 77A, 77B, 78A, 78B, 79A, 79B, 80A, and 80B.

The following compounds were found to have a Kdapp of 300 nM or less:
Compounds 1, 8, 9, 13, 19, 23, 24, 25, 27, 32, 38, 41, 43, 51, 60, 64, 66, 68, 71A, 71B, 72A, 72B, 73A, 73B, 74A, 74B, 75A, 75B, 76A, 76B, 77A, 77B, 78A, 78B, 79A, 79B, 80A, and 80B.

The following compounds were found to have a Kdapp of 100 nM or less:
Compounds 1, 8, 9, 13, 19, 23, 25, 32, 41, 43, 51, 60, 64, 66, 68, 71A, 71B, 72A, 72B, 73A, 73B, 74A, 74B, 75A, 75B, 76A, 76B, 77A, 77B, 78A, 78B, 79A, 79B, and 80A.

The following compounds were found to have a Kdapp of 30 nM or less:
Compounds 8, 9, 13, 19, 23, 25, 41, 51, 64, 68, 71A, 71B, 72A, 73A, 74A, 74B, 76A, 77A, 77B, 79B, and 79A.

Study 2

In Vivo Study

Animal Model with Reduction in the Size of the Sebaceous Glands

The model of the sebaceous gland of the ear of a Syrian hamster described by Plewig and Luderschmidt in *J. Inv. Derm.*, (1977), pp. 171-176 is a classical tool for the in vivo study of the function of the sebaceous gland. In fact, the inner faces of the ear lobes of the hamster contain a high number of sebaceous glands described as being similar to those of human sebaceous follicles in terms of certain characteristics, including their morphology and response to androgens and anti-androgens. In fact the growth and lipogenesis of the sebaceous glands on the inner face of the ear of Syrian hamsters depend on the androgens. The anti-androgenic activity of test compounds can be easily evaluated by measuring the size of the sebaceous glands. Moreover, this model has been selected to evaluate the efficacy of the antagonists of the receptor to the androgens on the sebaceous gland.

Test compounds were evaluated according to the following protocol: male hamsters aged weeks were treated daily for 24 days on the inner face of the right ear with 30 μL of a solution of the test compound to be evaluated in absolute ethanol. For each test compound, groups were treated with solutions at a range of concentrations (e.g., from 0.01 g %/mL to 3 g %/mL), as well as absolute ethanol used as a control. (A concentration of 3 g %/mL means a concentration of 0.03 g/mL.)

At the end of the study, samples were taken from the treated ears. The skin of the inner face of the ear was separated from the cartilage. Under a binocular magnifying glass, two zones of 4 mm² were numbered. The size of the sebaceous glands was measured on the numerical images by manually trimming the glands by means of image analysis software (TINA.20). For each image some twenty glands were measured. The average area of the sebaceous glands was calculated for each treatment group.

A Student t-test for independent groups comparing each dose with vehicle was carried out to compare the average size of the sebaceous glands as a function of the doses applied. When the evolution of the effect is represented graphically as a function of the administered dose of test compound, the curve obtained is sigmoid in shape. In the median part, this sigmoid may be likened to a straight line. The dose corresponding to 50% of the maximum effect corresponds graphically to the point located in the centre of the linear section defined as "effective dose 50". This $DE_{50}$ characterises the potency of the test compound.

Results obtained in this test for certain compounds described herein are shown in Table 4. For example, for Compound 1, 50% of the maximum effect was observed at a concentration of 0.2 g %/mL.

The percent reduction in the size of the sebaceous glands observed following treatment with a 1 g %/mL solution of test compound, as compared to the control, are also shown in Table 4. For example, for Compound 1, a concentration of 1 g %/mL caused a 53% reduction in the size of the sebaceous glands as compared to control.

TABLE 4

| Compound No. | $DE_{50}$ (g %/mL) | Reduction of sebaceous glands (following treatment at 1 g %/mL) |
|---|---|---|
| 1 | 0.20 | 53% |
| 8 | 0.10 | 56% |
| 19 | 0.07 | 61% |
| 23 | 0.04 | 51% |
| 41 | 0.04 | 61% |
| 43 | 0.20 | 44% |
| 68 | 0.04 | 57% |
| 71B | 0.04 | 56% |
| 72A | 0.06 | 48% |
| 72B | 0.26 | 46% |
| 74B | 0.01 | 61% |
| 76A | 0.02 | 58% |
| 78B | 0.04 | 50% |
| 79A | 0.04 | 48% |
| 80A | 0.20 | 51% |

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. A compound of formula (1), or a pharmaceutically acceptable salt, hydrate, or solvate thereof:

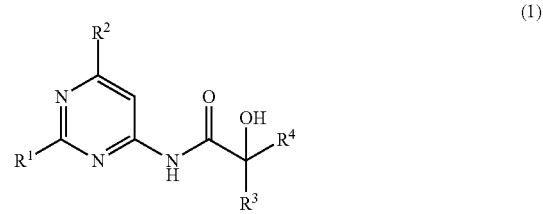

(1)

wherein:
R¹ is $C_{1-6}$ alkyl, $C_{3-7}$ cycloalkyl, $C_{1-6}$ alkyloxy, —S(O)$_m$—$C_{1-6}$ alkyl, $C_{1-6}$ fluoroalkyl, $C_{1-6}$ fluoroalkyloxy, $C_{1-6}$ alkyl-OH, —(CH$_2$)$_i$—$C_{1-6}$ alkyloxy, —(CH$_2$)$_j$—O—$C_{1-6}$ fluoroalkyl, COR$^a$, CN, NO$_2$, NR$^5$R$^6$, or a halogen atom;

R² is a hydrogen atom, $C_{1-6}$ alkyl, $C_{3-7}$ cycloalkyl, $C_{1-6}$ alkyloxy, —S(O)$_n$—$C_{1-6}$ alkyl, $C_{1-6}$ fluoroalkyl, $C_{1-6}$ fluoroalkyloxy, $C_{1-6}$ alkyl—OH, —(CH$_2$)$_k$—$C_{1-6}$ alkyloxy, —(CH$_2$)$_l$—O—$C_{1-6}$ fluoroalkyl, COR$^b$, CN, NO$_2$, NR$^{5'}$R$^{6'}$, OH, or a halogen atom, and at least one of R¹ and R² is $C_{1-6}$ alkyloxy;

R³ and R⁴ are identical or different and are a hydrogen atom, $C_{1-12}$ alkyl, $C_{3-9}$ cycloalkyl, $C_{1-6}$ fluoroalkyl, —$C_{1-6}$ alkyl—OH, —(CH$_2$)$_p$—$C_{1-6}$ alkyloxy, —(CH$_2$)$_q$—$C_{3-9}$ cycloalkyl, —(CH$_2$)$_r$—$C_{1-6}$ fluoroalkyl, —(CH$_2$)$_s$—O—$C_{1-6}$ fluoroalkyl, phenyl, heteroaryl, heterocyclyl group, —(CH$_2$)$_t$-phenyl, or —(CH$_2$)$_v$-heteroaryl, wherein each phenyl and heteroaryl is optionally substituted with one to three identical or different R$^c$ groups;

or R$^3$ and R$^4$, together with the carbon atom carrying them, may form a C$_{3-9}$ cycloalkyl group or a heterocyclyl group, wherein the heterocylyl group is selected from tetrahydrofuranyl, tetrahydropyranyl, tetrahydrothiopyranyl, tetrahydro-1-oxo-thiopyranyl, or tetrahydro-1,1-dioxo-thiopyranyl;

R$^c$ is C$_{1-6}$ alkyl, C$_{3-7}$ cycloalkyl, C$_{1-6}$ alkyloxy, —S(O)$_u$—C$_{1-6}$ alkyl, C$_{1-6}$ fluoroalkyl, C$_{1-6}$ fluoroalkyloxy, C$_{1-6}$ alkyl-OH, COR$^d$, CN, NO$_2$, NR$^9$R$^{10}$, OH, or a halogen atom;

R$^a$, R$^b$, and R$^d$ are identical or different and are C$_{1-6}$ alkyl, C$_{1-6}$ alkyloxy, or NR$^7$R$^8$;

R$^5$, R$^{5'}$, R$^6$, R$^{6'}$, R$^7$, R$^8$, R$^9$ and R$^{10}$ are identical or different and are a hydrogen atom, C$_{1-6}$ alkyl, C$_{3-7}$ cycloalkyl, or —(CH$_2$)$_w$—C$_{3-7}$ cycloalkyl;

wherein R$_5$ and R$_6$, together with the nitrogen atom carrying them, may form a heterocyclyl group;

wherein R$_5$' and R$_6$', together with the nitrogen atom carrying them, may form a heterocyclyl group;

wherein R$_7$ and R$_8$, together with the nitrogen atom carrying them, may form a heterocyclyl group;

wherein R$_9$ and R$_{10}$, together with the nitrogen atom carrying them, may form a heterocyclyl group;

i, j, k, l, p, q, r, s, t, v, and w are different or identical and are 1, 2 or 3; and m, n, and u are different or identical and are 0, 1 or 2.

2. The compound according to claim 1, wherein at least one of R$^1$ and R$^2$ is methoxy.

3. The compound according to claim 1, the compound being one of 2-Hydroxy-2-methyl-pentanoic acid (2,6-dimethoxy-pyrimidin-4-yl)-amide and N-(2-Bromo-6-methoxy-pyrimidin-4-yl)-2-ethyl-2-hydroxy-butyramide.

4. The compound according to claim 2, the compound being 2-Hydroxy-2-methyl-pentanoic acid (2,6-dimethoxy-pyrimidin-4-yl)-amide.

5. The compound according to claim 2, the compound being N-(2-Bromo-6-methoxy-pyrimidin-4-yl)-2-ethyl-2-hydroxy-butyramide.

6. A composition comprising a compound according to claim 1, and a carrier, diluent, or excipient.

7. A pharmaceutical composition comprising a compound according to claim 1, and a pharmaceutically acceptable carrier, diluent, or excipient.

8. A method of preparing a pharmaceutical composition, the method comprising a step of mixing a compound according to claim 1 and a pharmaceutically acceptable carrier, diluent, or excipient.

9. A method of treating a dermatological disease or disorder; the method comprising administering an effective amount of the compound according to claim 1 to an individual subject in need thereof, wherein the disease or disorder is selected from the group consisting of a disease or disorder of the sebaceous gland(s), acne, hyperseborrhoea, oily skin, seborrhoeic dermatitis, and atopic dermatitis.

10. A method of treating a dermatological disease or disorder; the method comprising administering a therapeutically-effective amount of a compound according to claim 1 to a patient in need of said treatment, wherein the disease or disorder is selected from the group consisting of a disease or disorder of the sebaceous gland(s), acne, hyperseborrhoea, oily skin, seborrhoeic dermatitis, and atopic dermatitis.

11. A method of treating acne, the method comprising administering a therapeutically-effective amount of a compound according to claim 1 to a patient in need of said treatment.

12. A cosmetic composition comprising a compound according to claim 1, and a cosmetic carrier, diluent, or excipient.

13. The cosmetic composition according to claim 12, wherein the composition is in the form of an ointment, a cream, a milk, a pomade, a gel, a suspension, lipidic or polymeric blisters or polymeric or gelled patches allowing controlled release, a powder, a lipidic or polymeric blister, an alcohol swab, a syndet, a solution, a spray, a mousse, a stick, a soap, a cleansing base, or a shampoo.

14. A non-therapeutic method of body care and/or hair care, the method comprising applying to the body and/or hair of a subject an effective amount of a compound according to claim 1.

15. A non-therapeutic method of body care and/or hair care, the method comprising administering an effective amount of the compound according to claim 1 to an individual subject in need thereof.

16. A method of making a cosmetic composition for use in a non-therapeutic method of body care and/or hair care, the method comprising making the composition with an effective amount of the compound according to claim 1.

17. A non-therapeutic method of body care and/or hair care, the method comprising applying to the body and/or hair of a subject an effective amount of a cosmetic composition comprising a compound according to claim 1.

18. A non-therapeutic method of body care and/or hair care, the method comprising administering a cosmetic composition comprising an effective amount of the compound according to claim 1 to an individual subject in need thereof.

* * * * *